United States Patent
Han et al.

(10) Patent No.: US 11,542,237 B2
(45) Date of Patent: Jan. 3, 2023

(54) FLUORENE DERIVATIVE AND ORGANIC LIGHT EMITTING DEVICE COMPRISING SAME

(71) Applicant: LG CHEM, LTD., Seoul (KR)

(72) Inventors: Miyeon Han, Daejeon (KR); Dong Hoon Lee, Daejeon (KR); Jungoh Huh, Daejeon (KR); Boonjae Jang, Daejeon (KR); Dong Uk Heo, Daejeon (KR); Junghoon Yang, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 355 days.

(21) Appl. No.: 16/629,296

(22) PCT Filed: Jul. 23, 2018

(86) PCT No.: PCT/KR2018/008281
§ 371 (c)(1),
(2) Date: Jan. 7, 2020

(87) PCT Pub. No.: WO2019/022455
PCT Pub. Date: Jan. 31, 2019

(65) Prior Publication Data
US 2020/0131138 A1 Apr. 30, 2020

(30) Foreign Application Priority Data
Jul. 28, 2017 (KR) .................. 10-2017-0096142

(51) Int. Cl.
*C07D 239/26* (2006.01)
*C07D 251/14* (2006.01)
(Continued)

(52) U.S. Cl.
CPC ......... *C07D 239/26* (2013.01); *C07D 251/14* (2013.01); *H01L 51/0052* (2013.01);
(Continued)

(58) Field of Classification Search
CPC ............... C07D 239/26; C07D 251/14; H01L 51/0052; H01L 51/0067; H01L 51/5056; H01L 51/5072; H01L 51/5092
See application file for complete search history.

(56) References Cited

U.S. PATENT DOCUMENTS 10,381,572 B2   8/2019  Jang et al.
2006/0154384 A1  7/2006  Murphy et al.
(Continued)

FOREIGN PATENT DOCUMENTS

CN   1689173      10/2005
CN   106164216 A  11/2016
(Continued)

OTHER PUBLICATIONS

Computer-generated English-language translation of KR-20170134264-A.*
(Continued)

*Primary Examiner* — Vu A Nguyen
(74) *Attorney, Agent, or Firm* — Dentons US LLP

(57) ABSTRACT

Provided is a fluorene derivative of Chemical Formula 1:

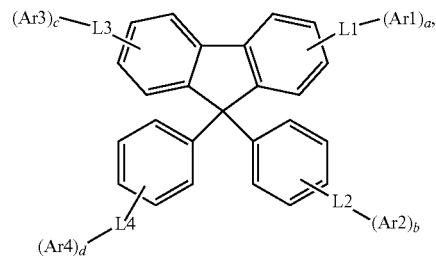

and an organic light emitting device comprising the same.

13 Claims, 1 Drawing Sheet

(51) Int. Cl.
*H01L 51/00* (2006.01)
*H01L 51/50* (2006.01)

(52) U.S. Cl.
CPC ...... *H01L 51/0067* (2013.01); *H01L 51/5056* (2013.01); *H01L 51/5072* (2013.01); *H01L 51/5092* (2013.01)

(56) References Cited

U.S. PATENT DOCUMENTS

| | | |
|---|---|---|
| 2014/0001451 A1 | 1/2014 | Mizuki et al. |
| 2015/0162543 A1 | 6/2015 | Lee et al. |
| 2018/0222872 A1 | 8/2018 | Jatsch et al. |
| 2019/0207120 A1 | 7/2019 | Han et al. |
| 2021/0013422 A1 | 1/2021 | Heo et al. |

FOREIGN PATENT DOCUMENTS

| | | |
|---|---|---|
| CN | 106977468 A | 7/2017 |
| CN | 107353281 A | 11/2017 |
| CN | 109071465 A | 12/2018 |
| CN | 109790131 A | 5/2019 |
| CN | 110622332 | 12/2019 |
| EP | 3127901 A1 | 2/2017 |
| KR | 10-20120052499 | 5/2012 |
| KR | 10-20140128879 | 11/2014 |
| KR | 10-20140130967 | 11/2014 |
| KR | 10-1542714 | 8/2015 |
| KR | 10-20150136032 | 12/2015 |
| KR | 20150136032 A * | 12/2015 |
| KR | 10-20170134264 | 12/2017 |
| KR | 20170134264 A * | 12/2017 |
| WO | 2013-175789 | 11/2013 |
| WO | 2017-016630 | 2/2017 |
| WO | WO-2017171376 A1 * | 10/2017 ........... C07C 13/567 |

OTHER PUBLICATIONS

Computer-generated English-language translation of KR-20150136032-A.*
Computer-generated English-language translation of WO-2017171376-A1.*

* cited by examiner

【FIG. 1】
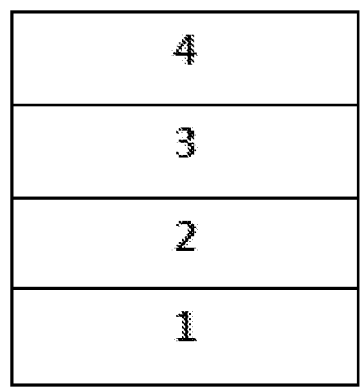
【FIG. 2】
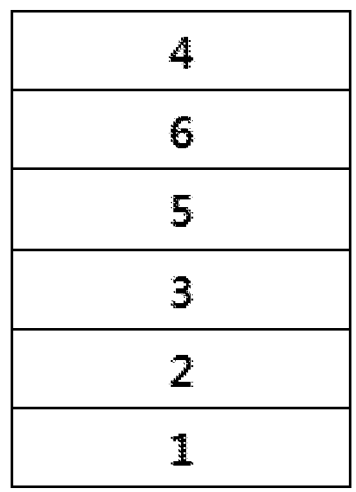

FLUORENE DERIVATIVE AND ORGANIC LIGHT EMITTING DEVICE COMPRISING SAME

CROSS-REFERENCE TO RELATED APPLICATION(S)

The present specification is a National Stage Application of International Application No. PCT/KR2018/008281 filed on Jul. 23, 2018, which claims priority to and the benefits of Korean Patent Application No. 10-2017-0096142, filed with the Korean Intellectual Property Office on Jul. 28, 2017, the entire contents of which are incorporated herein by reference.

TECHNICAL FIELD

The present specification relates to a fluorene derivative and an organic light emitting device including the same.

BACKGROUND

In general, organic light emission refers to a phenomenon in which electrical energy is converted into light energy using an organic material. An organic light emitting device using the phenomenon of organic light emission generally has a structure including an anode, a cathode and an organic material layer interposed therebetween. Here, the organic material layer generally has a structure including a plurality of layers composed of different materials in order to improve efficiency and stability of the organic light emitting device and may, for example, include a hole injection layer, a hole transport layer, a light emitting layer, an electron transport layer, an electron injection layer and the like. In such a structure of the organic light emitting device, when a voltage is applied between two electrodes, holes and electrons are injected into the organic material layer from the anode and the cathode, respectively, and the injected holes and electrons are combined to form excitons. When the excitons fall to the ground state again, light is emitted.

There is a continuous need for development of novel materials for the aforementioned organic light emitting device.

Technical Problem

The present specification is directed to providing a fluorene derivative and an organic light emitting device including the same.

Technical Solution

One embodiment of the present specification provides a fluorene derivative of Chemical Formula 1:

[Chemical Formula 1]

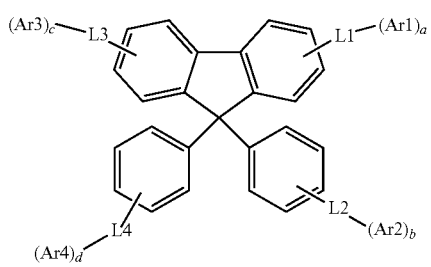

wherein L1 to L4 are identical to or different from one another, and are each independently a direct bond, a substituted or unsubstituted arylene group, or a substituted or unsubstituted heteroarylene group;

Ar1 and Ar2 are identical to or different from each other, and are each independently hydrogen, or a compound of the following Chemical Formula 2, wherein at least one of Ar1 and Ar2 is the compound of the following Chemical Formula 2;

Ar3 and Ar4 are identical to or different from each other, and are each independently hydrogen, or a compound of the following Chemical Formula 3, wherein at least one of Ar3 and Ar4 is the compound of the following Chemical Formula 3;

a and c are each an integer of 0 to 4; and
b and d are each an integer of 0 to 5, wherein, when a is a number of 2 or more, Ar1 are identical to or different from each other, when b is a number of 2 or more, Ar2 are identical to or different from each other, when c is a number of 2 or more, Ar3 are identical to or different from each other, and when d is a number of 2 or more, Ar4 are identical to or different from each other,

[Chemical Formula 2]

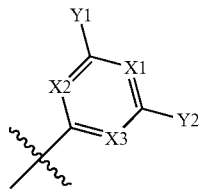

[Chemical Formula 3]

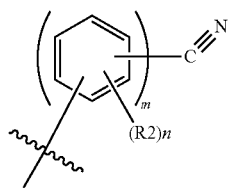

wherein:

is a moiety linked to the compound of Chemical Formula 1;

X1 to X3 are identical to or different from one another, and are each independently N or CR1, wherein two or more of X1 to X3 are N;

R1, R2, Y1 and Y2 are identical to or different from one another, and are each independently hydrogen, deuterium, a substituted or unsubstituted alkyl group, a substituted or unsubstituted silyl group, a substituted or unsubstituted alkoxy group, a substituted or unsubstituted aryl group, or a substituted or unsubstituted heteroaryl group, or are linked to an adjacent group to form a ring;

n is an integer of 0 to 4, in which, when n is 2 or more, R2 are identical to or different from each other; and m is 0 or 1.

In addition, another embodiment of the present specification provides an organic light emitting device including: a first electrode; a second electrode facing the first electrode; and at least one organic material layer interposed between the first electrode and the second electrode, wherein the at least one organic material layer contains the fluorene derivative of Chemical Formula 1.

Advantageous Effects

The fluorene derivative according to an embodiment of the present specification can be used as a material for an organic material layer in an organic light emitting device and thus can improve efficiency, lower driving voltage and/or lifetime characteristics of the organic light emitting device.

DESCRIPTION OF DRAWINGS

FIG. 1 illustrates an organic light emitting device according to an embodiment of the present specification.
FIG. 2 illustrates an organic light emitting device according to another embodiment of the present specification.
1: Substrate
2: First electrode
3: Organic material layer
4: Second electrode
5: Light emitting layer
6: Electron injection and transport layer

MODE FOR DISCLOSURE

Hereinafter, the present specification will be described in more detail.

The present specification provides the fluorene derivative of Chemical Formula 1.

It will be understood throughout the present specification that, when an element is referred to as "comprising" another element, the term "comprising" does not preclude the presence or addition of at least one other element and allows the presence or addition of other element, unless otherwise mentioned.

It will be understood throughout the present specification that, when an element is referred to as being "on" another element, it can directly contact the other element or an intervening element can also be present between the two elements.

According to the present specification, examples of substituents will be mentioned below, but the specification is not limited thereto.

The term "substitution" as used herein means that the hydrogen atom bonded to the carbon atom of a compound is changed to a different substituent, there is no limitation as to the position at which substitution occurs so long as it is the position at which the hydrogen atom is substituted, that is, the position at which substitution of the substituent is possible, and when two or more elements are substituted, the two or more substituents can be identical to or different from one another.

The term "substituted or unsubstituted" as used herein means that an element is substituted by one or more substituents selected from the group consisting of deuterium, a nitrile group, a substituted or unsubstituted alkyl group, a substituted or unsubstituted cycloalkyl group, a substituted or unsubstituted silyl group, a substituted or unsubstituted aryl group, and a substituted or unsubstituted heterocyclic group, or an element is substituted by a substituent, to which two or more substituents among the exemplified substituents are linked, or an element has no substituent. For example, "a substituent to which two or more substituents are linked" can mean an aryl group substituted by an aryl group, an aryl group substituted by a heteroaryl group, a heterocyclic group substituted by an aryl group, an aryl group substituted by an alkyl group, or the like.

According to the present specification, the alkyl group can be a linear or branched chain, and the number of carbon atoms thereof is not particularly limited, but is preferably 1 to 30. Specifically, examples of the alkyl group include, but are not limited to, methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl and the like.

According to the present specification, the number of carbon atoms of the cycloalkyl group is not particularly limited, but is preferably 3 to 30. Specifically, examples of cycloalkyl group include, but are not limited to, cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethyl-cyclohexyl, 3,4,5-trimethylcyclohexyl, 4-tert-butylcyclohexyl, cycloheptyl, cyclooctyl and the like.

According to the present specification, examples of the silyl group include, but are not limited to, a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like.

According to the present specification, the number of carbon atoms of the aryl group is not particularly limited, but is preferably 6 to 30. The aryl group can be monocyclic or polycyclic.

When the aryl group is a monocyclic aryl group, the number of carbon atoms thereof is not particularly limited, but is preferably 6 to 30. Specifically, examples of the monocyclic aryl group include, but are not limited to, a phenyl group, a biphenyl group, a terphenyl group and the like.

When the aryl group is a polycyclic aryl group, the number of carbon atoms thereof is not particularly limited, but is preferably 10 to 30. Specifically, examples of the polycyclic aryl group include, but are not limited to, a naphthyl group, an anthracenyl group, a phenanthryl group, a triphenyl group, a pyrenyl group, a phenalenyl group, a perylenyl group, a chrysenyl group, a fluorenyl group and the like.

According to the present specification, the fluorenyl group can be substituted and adjacent groups can be linked to each other to form a ring.

When the fluorenyl group is substituted, it can be

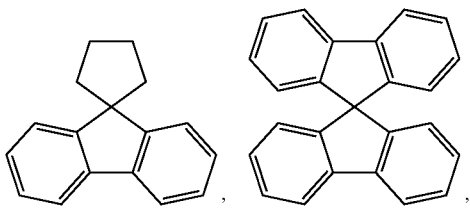

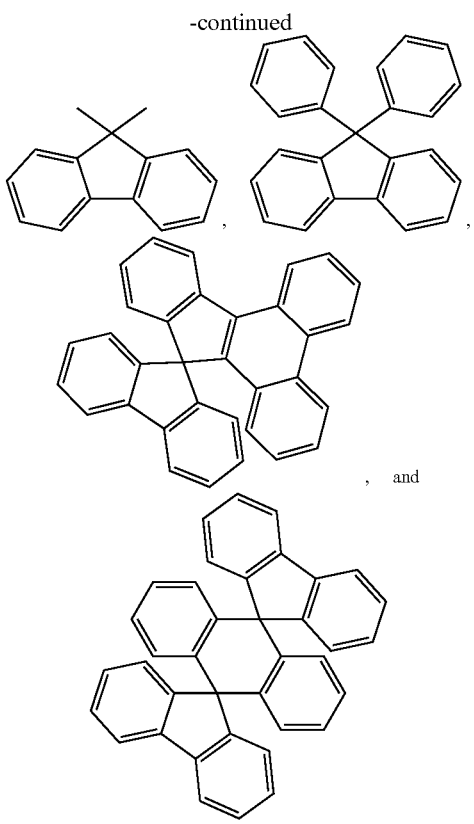

, and

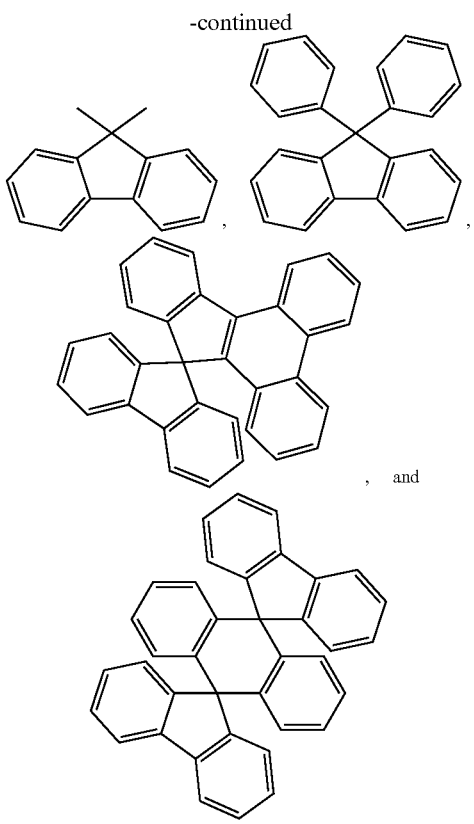

or the like, but is not limited thereto.

According to the present specification, the heteroaryl group includes at least one heteroatom which means an atom excluding carbon. Specifically, the heteroatom can include at least one atom selected from the group consisting of O, N, Se, S and the like. The number of carbon atoms of the heteroatom is not particularly limited, but is preferably 2 to 30. The heteroaryl group can be monocyclic or polycyclic. Examples of the heterocyclic group include, but are not limited to, a thiophene group, a furanyl group, a pyrrolyl group, an imidazolyl group, a triazolyl group, an oxazolyl group, an oxadiazolyl group, a pyridyl group, a bipyridyl group, a pyrimidyl group, a triazinyl group, a thiadiazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthrolinyl group, an isoxazolyl group, a thiadiazolyl group, a phenothiazinyl group, a dibenzofuranyl group and the like.

According to the present specification, the arylene group is defined as in the aryl group, except that the arylene group is bivalent.

According to the present specification, the heteroarylene group is defined as in the heteroaryl group, except that the heteroarylene group is bivalent.

According to an embodiment of the present specification, in Chemical Formula 3, the CN group can be substituted at the 2 position, when the moiety linked to L3 or L4 is the 1 position.

According to an embodiment of the present specification, in Chemical Formula 3, the CN group can be substituted at the 3 position, when the moiety linked to L3 or L4 is the 1 position.

According to an embodiment of the present specification, in Chemical Formula 3, the CN group can be substituted at the 4 position, when the moiety linked to L3 or L4 is the 1 position.

According to an embodiment of the present specification, the fluorene derivative of Chemical Formula 1 can be any one selected from the compounds of the following Chemical Formulae A and B:

[Chemical Formula A]

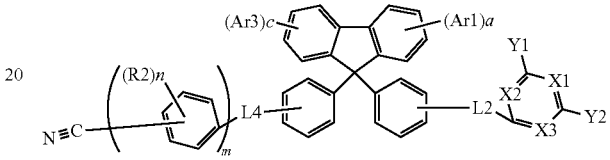

[Chemical Formula B]

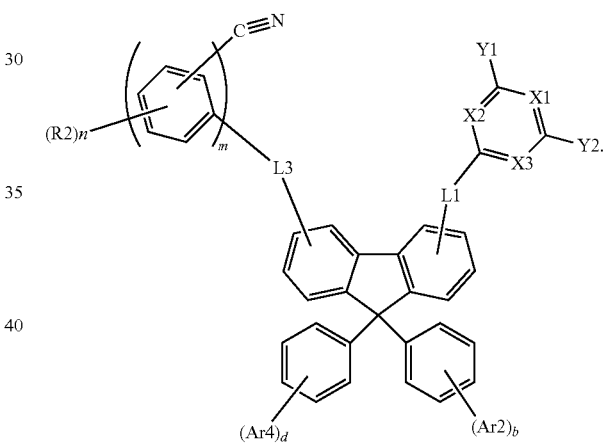

In Chemical Formulae A and B, Ar1 to Ar4, R2, a to d, X1 to X3, Y1, Y2, L1 to L4, n and m are defined as in Chemical Formulae 1 to 3 above.

According to an embodiment of the present specification, the fluorene derivative of Chemical Formula 1 can be any one of compounds of the following Chemical Formulae 4 to 9:

[Chemical Formula 4]

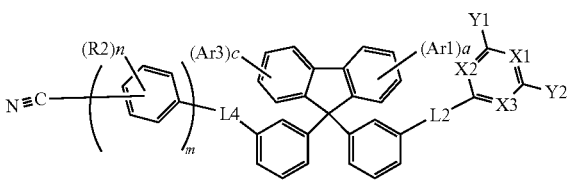

[Chemical Formula 5]

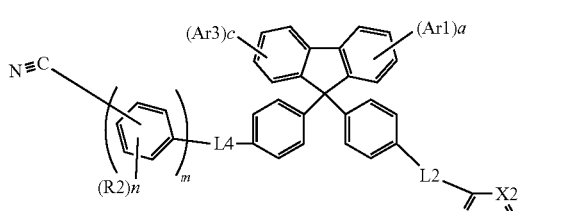

[Chemical Formula 6]

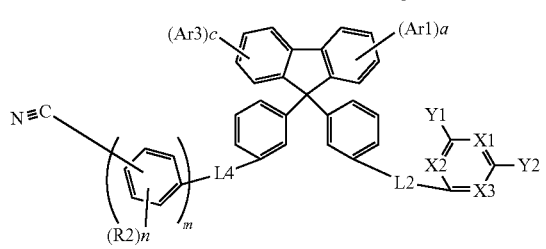

[Chemical Formula 7]

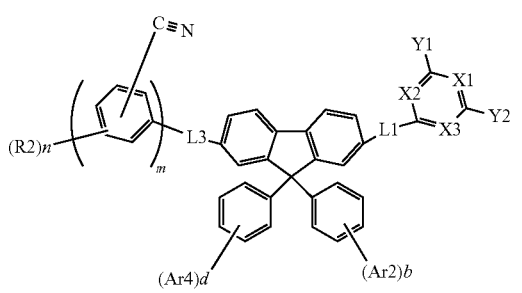

[Chemical Formula 8]

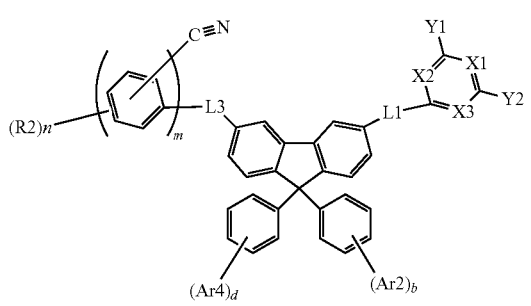

[Chemical Formula 9]

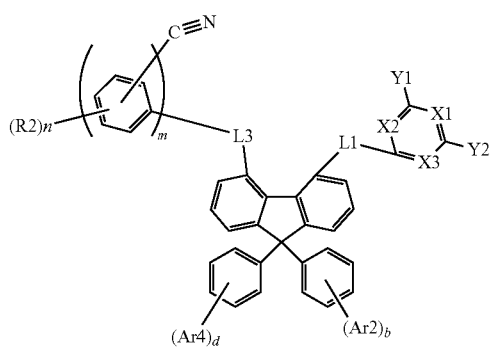

wherein Ar1 to Ar4, R2, a to d, X1 to X3, Y1, Y2, L1 to L4, n and m are defined as in Chemical Formulae 1 to 3 above.

According to an embodiment of the present specification, Ar1 and Ar2 are identical to or different from each other, and are each independently hydrogen or the compound of Chemical Formula 2.

According to an embodiment of the present specification, Ar1 and Ar2 are hydrogen.

According to an embodiment of the present specification, Ar1 and Ar2 are identical to each other and are the compound of Chemical Formula 2.

According to an embodiment of the present specification, Ar1 is hydrogen and Ar2 is the compound of Chemical Formula 2.

According to an embodiment of the present specification, Ar1 is the compound of Chemical Formula 2 and Ar2 is hydrogen.

According to an embodiment of the present specification, Ar3 and Ar4 are identical to or different from each other, and are each independently hydrogen or the compound of Chemical Formula 3.

According to an embodiment of the present specification, Ar3 and Ar4 are hydrogen.

According to an embodiment of the present specification, Ar3 and Ar4 are identical to each other, and are the compound of Chemical Formula 3.

According to an embodiment of the present specification, Ar3 is hydrogen and Ar4 is the compound of Chemical Formula 3.

According to an embodiment of the present specification, the Ar3 is the compound of Chemical Formula 3 and Ar4 is hydrogen.

According to an embodiment of the present specification, X1 to X3 are identical to or different from one another, and are each independently N or CR1.

According to an embodiment of the present specification, at least two of X1 to X3 are N.

According to an embodiment of the present specification, R1, R2, Y1 and Y2 are identical to or different from one another, and are each independently hydrogen, deuterium, a substituted or unsubstituted alkyl group, a substituted or unsubstituted silyl group, a substituted or unsubstituted alkoxy group, a substituted or unsubstituted aryl group, or a substituted or unsubstituted heteroaryl group, or are linked to an adjacent group to form a ring.

According to an embodiment of the present specification, R1 and R2 are hydrogen.

According to an embodiment of the present specification, R2 is linked to an adjacent group to form a ring.

According to an embodiment of the present specification, R2 is linked to an adjacent group to form an aromatic ring.

According to an embodiment of the present specification, R2 is linked to an adjacent group to form an aromatic ring having 6 to 30 carbon atoms.

According to an embodiment of the present specification, Y1 and Y2 are identical to or different from each other, and are each independently hydrogen, deuterium, or a substituted or unsubstituted aryl group.

According to an embodiment of the present specification, Y1 and Y2 are identical to or different from each other, and are each independently a substituted or unsubstituted aryl group having 6 to 20 carbon atoms.

According to an embodiment of the present specification, Y1 and Y2 are identical to or different from each other, and are each independently an aryl group having 6 to 20 carbon atoms substituted or unsubstituted by an alkyl group.

According to an embodiment of the present specification, Y1 and Y2 are identical to or different from each other, and are each independently a phenyl group substituted or unsubstituted by an alkyl group having 1 to 10 carbon atoms; or a biphenyl group.

According to an embodiment of the present specification, Y1 and Y2 are identical to or different from each other and are each independently a phenyl group substituted or unsubstituted by a methyl group; or a biphenyl group.

According to an embodiment of the present specification, L1 and L2 are identical to or different from each other and are each independently a phenylene group substituted or unsubstituted by an alkyl group; or a naphthylene group.

According to an embodiment of the present specification, L1 and L2 are identical to or different from each other and are each independently a phenylene group substituted or unsubstituted by an alkyl group having 1 to 10 carbon atoms; or a naphthylene group.

According to an embodiment of the present specification, L3 and L4 are identical to or different from each other, and are each independently a direct bond, a substituted or unsubstituted phenylene group, a substituted or unsubstituted biphenylene group, a substituted or unsubstituted naphthylene group, a substituted or unsubstituted phenanthrene group, a divalent fluorene group substituted or unsubstituted by an alkyl group, or a divalent fluorene group substituted or unsubstituted by an aryl group.

According to an embodiment of the present specification, L3 and L4 are identical to or different from each other, and are each independently a direct bond, a phenylene group, a biphenylene group, a naphthylene group, a phenanthrene group, or a divalent fluorene group substituted or unsubstituted by an alkyl group having 1 to 10 carbon atoms.

According to an embodiment of the present specification, the L3 and L4 are identical to or different from each other, and are each independently a direct bond, a phenylene group, a biphenylene group, a naphthylene group, a phenanthrene group, or a divalent dimethylfluorene group.

According to an embodiment of the present specification, L1 to L4 are identical to or different from one another, and are each independently a direct bond, a substituted or unsubstituted arylene group, or a substituted or unsubstituted heteroarylene group.

According to an embodiment of the present specification, L1 to L4 are identical to or different from one another, and are each independently a direct bond, a substituted or unsubstituted arylene group having 6 to 20 carbon atoms, or a substituted or unsubstituted, monocyclic or polycyclic heteroarylene group.

According to an embodiment of the present specification, L1 to L4 are identical to or different from one another, and are each independently a direct bond or any one of the following substituents.

According to an embodiment of the present specification, L1 to L4 are identical to or different from each other and are each independently a direct bond, a phenylene group, a biphenylene group or a naphthalene group.

According to an embodiment of the present specification, Chemical Formula 2 is a triazine group substituted or unsubstituted by an aryl group having 6 to 20 carbon atoms, or a pyrimidine group substituted or unsubstituted by an aryl group having 6 to 20 carbon atoms.

According to an embodiment of the present specification, Chemical Formula 2 is a triazine group or a pyrimidine group, and the triazine group or pyrimidine group is substituted or unsubstituted by a phenyl group, which is substituted or unsubstituted by an alkyl group, or by a biphenyl group, which is substituted or unsubstituted by an alkyl group.

According to an embodiment of the present specification, Chemical Formula 2 is a triazine group or a pyrimidine group, and the triazine group or pyrimidine group is substituted or unsubstituted by a phenyl group, which is substituted or unsubstituted by an alkyl group having 1 to 10 carbon atoms, or by a biphenyl group, which is substituted or unsubstituted by an alkyl group having 1 to 10 carbon atoms.

According to an embodiment of the present specification, Chemical Formula 2 is a triazine group or a pyrimidine group, and the triazine group or pyrimidine group is substituted or unsubstituted by a phenyl group, which is substituted or unsubstituted by a methyl group, or by a biphenyl group, which is substituted or unsubstituted by a methyl group.

According to an embodiment of the present specification, the fluorene derivative of Chemical Formula 1 is selected from the following compounds:

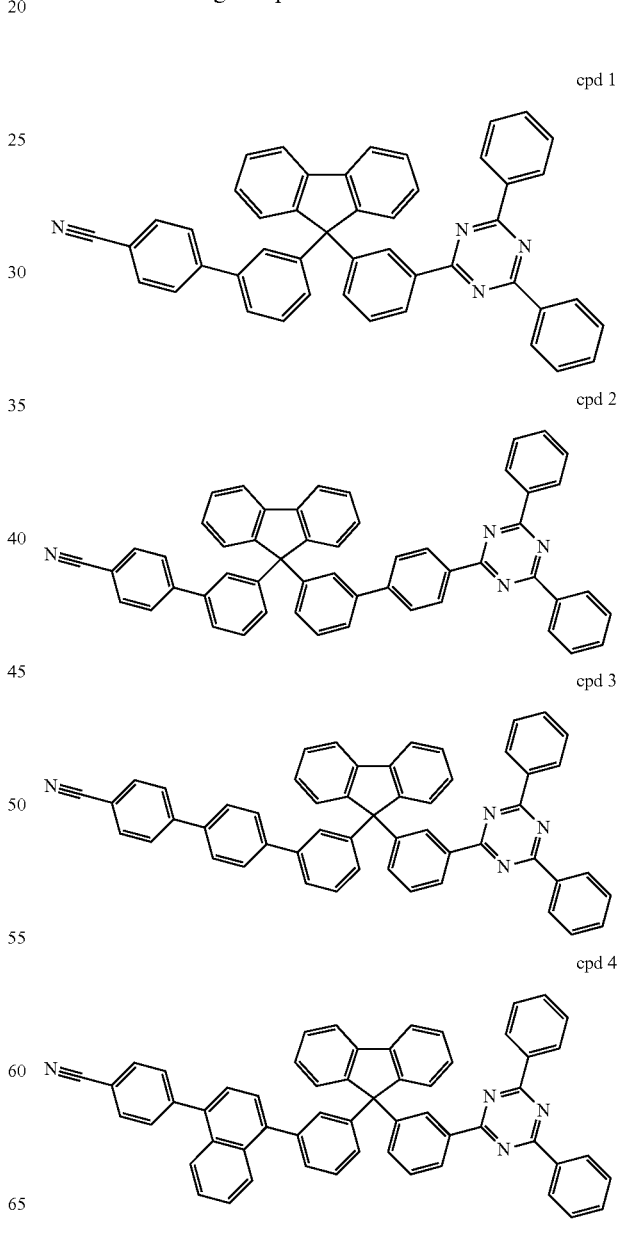

cpd 5
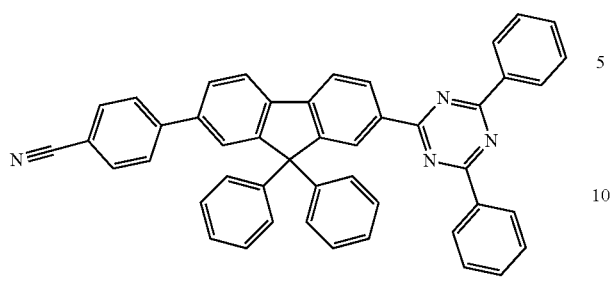
cpd 6
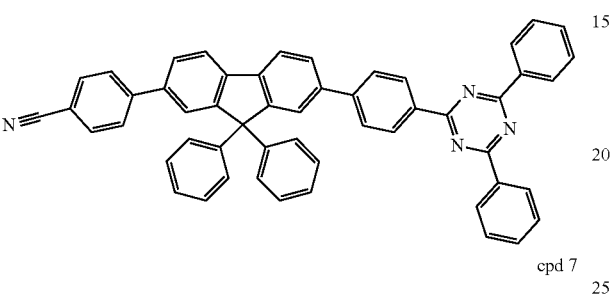
cpd 7
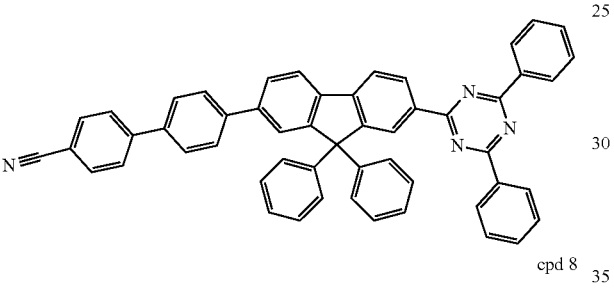
cpd 8
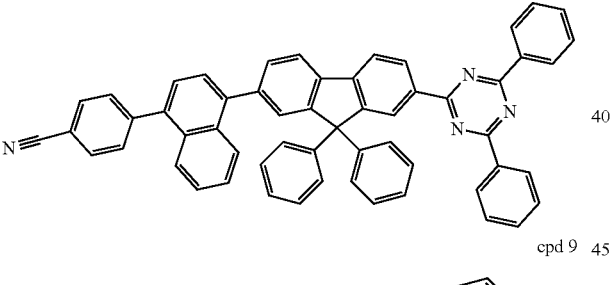
cpd 9
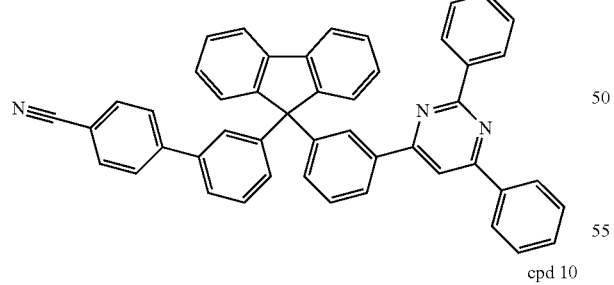
cpd 10
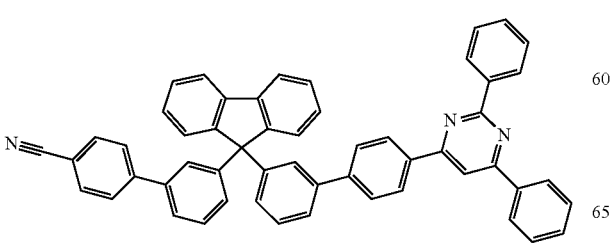
cpd 11
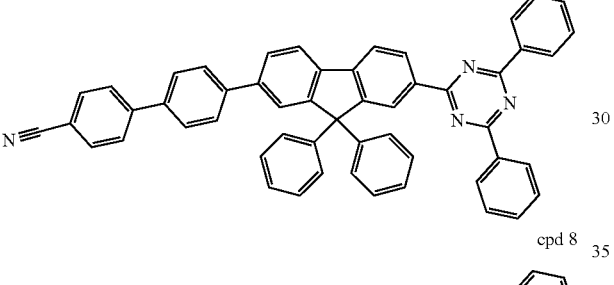
cpd 12
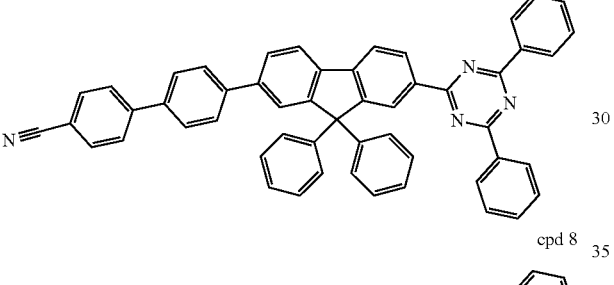
cpd 13
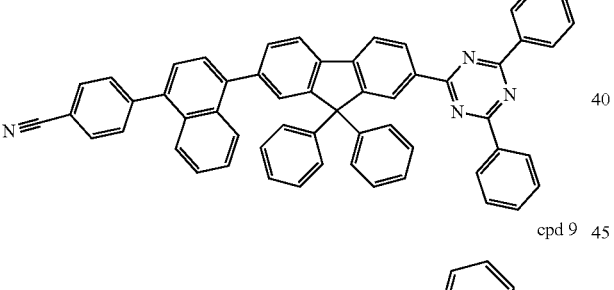
cpd 14
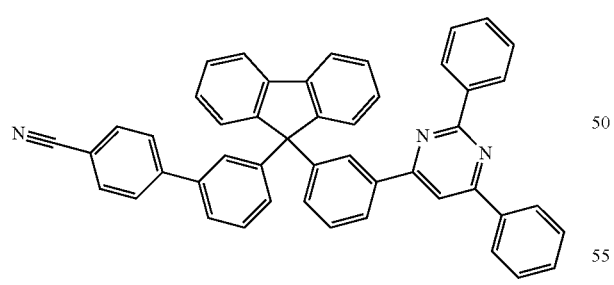
cpd 15
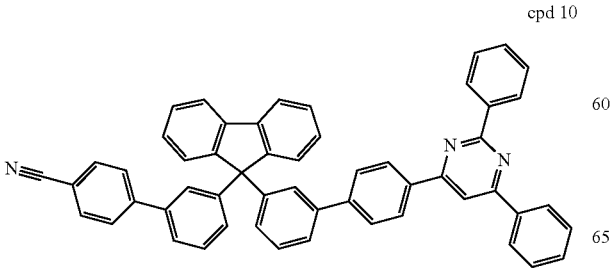
cpd 16
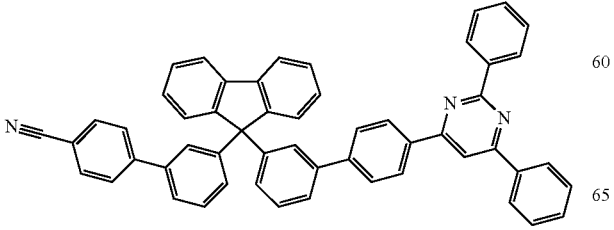

-continued
cpd 17
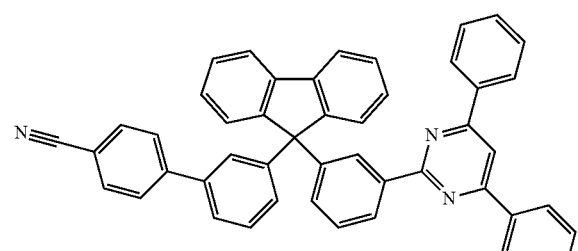
cpd 18
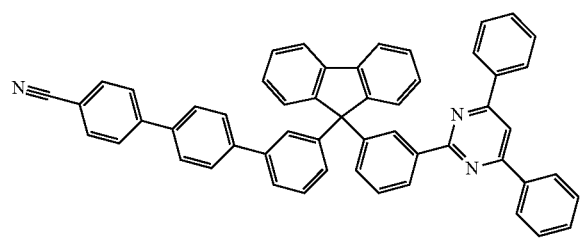
cpd 19
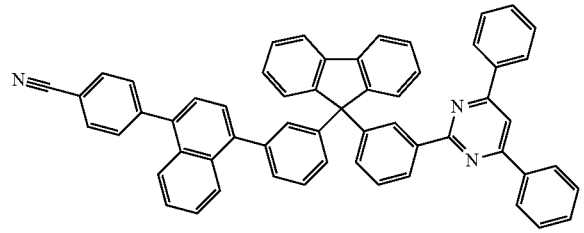
cpd 20
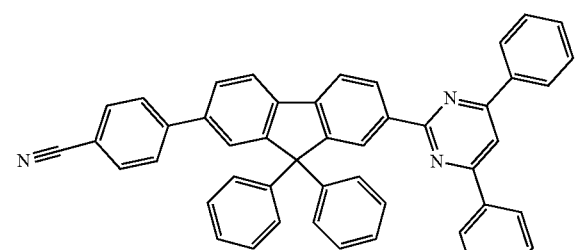
cpd 21
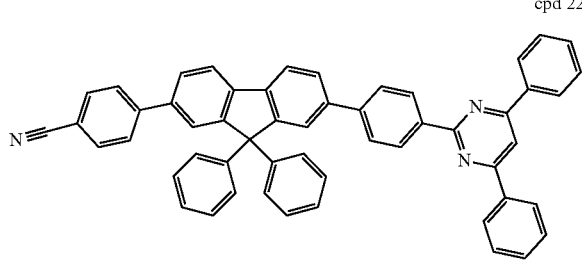
cpd 22
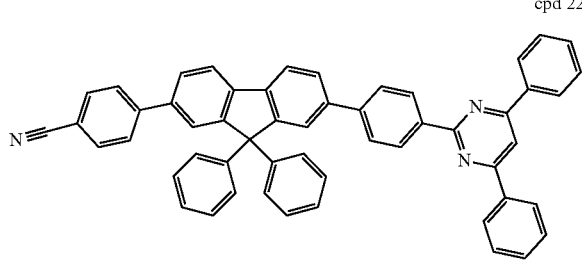
-continued
cpd 23
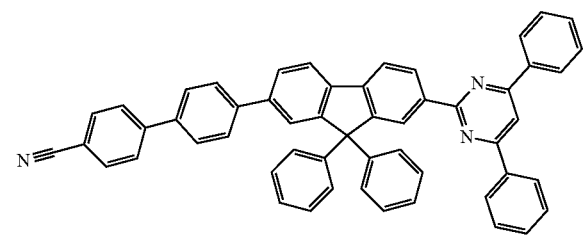
cpd 24
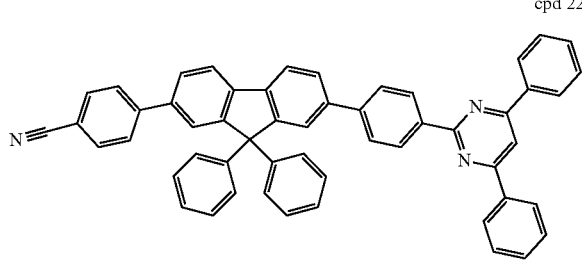
cpd 25
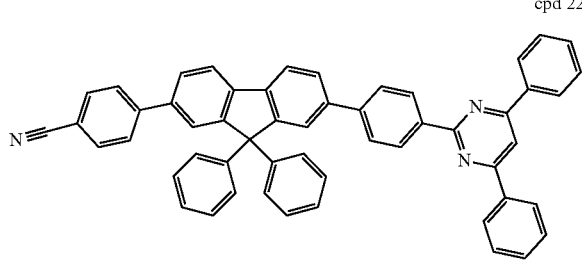
cpd 26
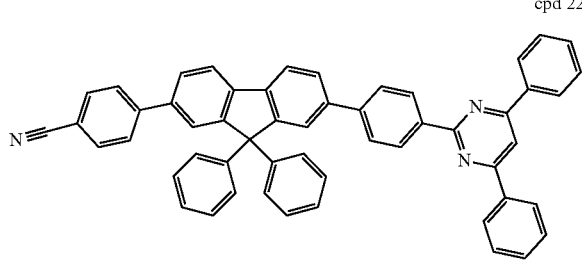
cpd 27
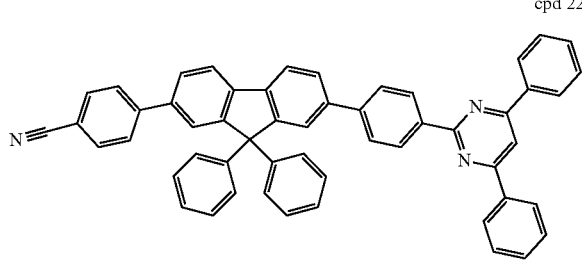

cpd 28
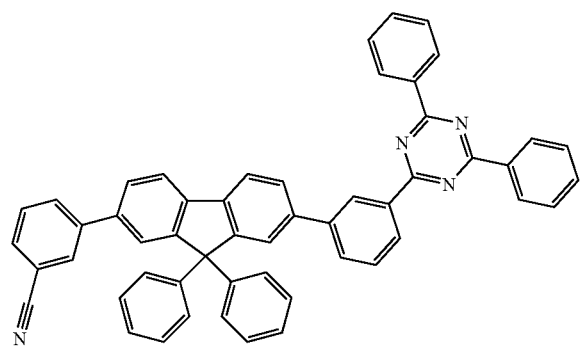
cpd 29
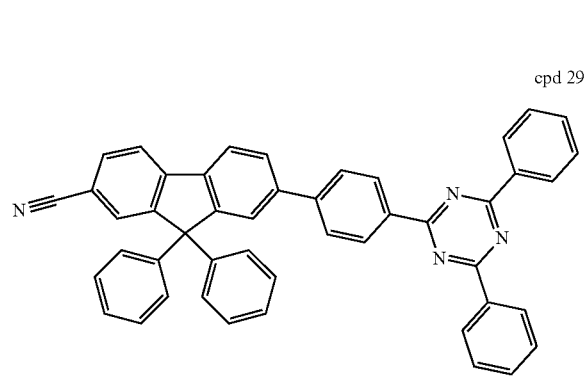
cpd 30
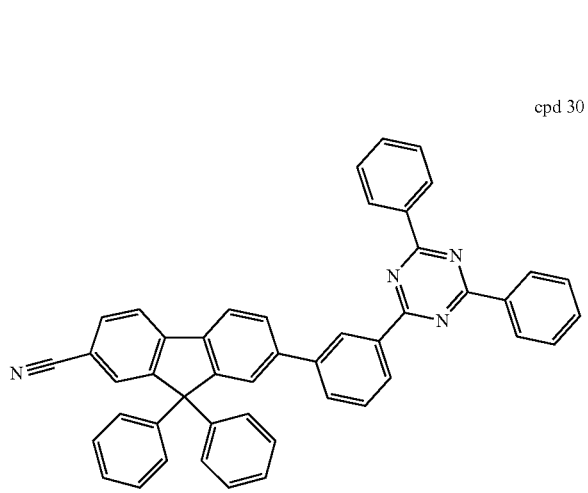
cpd 31
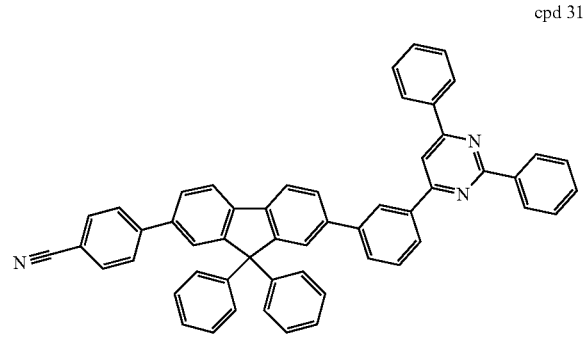
cpd 32
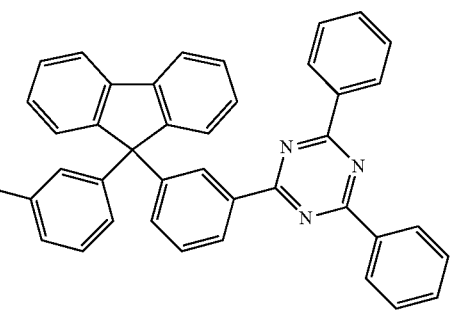
cpd 33
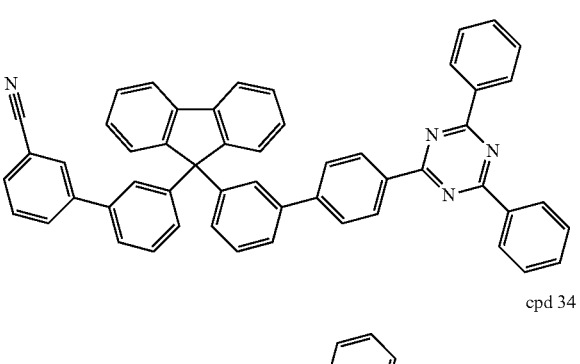
cpd 34
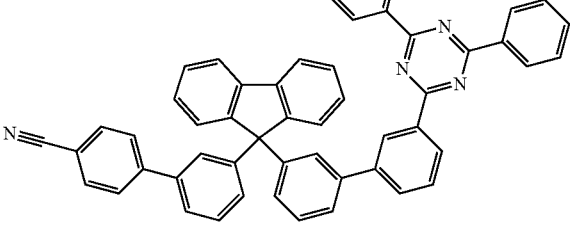
cpd 35
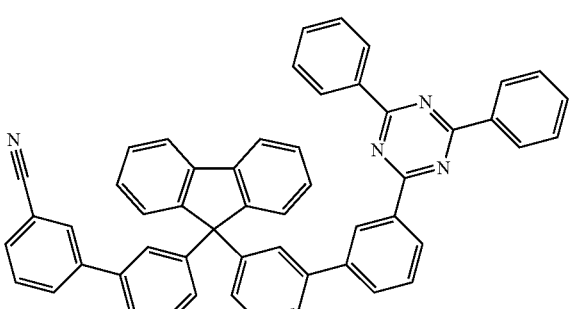
cpd 36
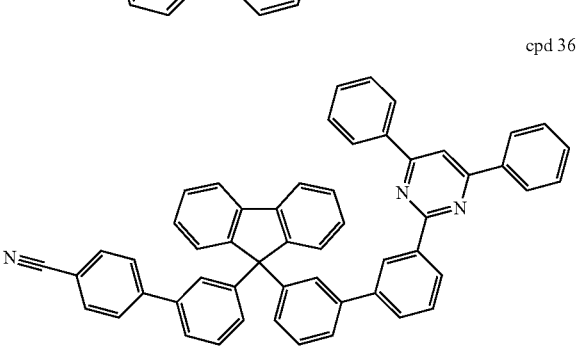

cpd 37
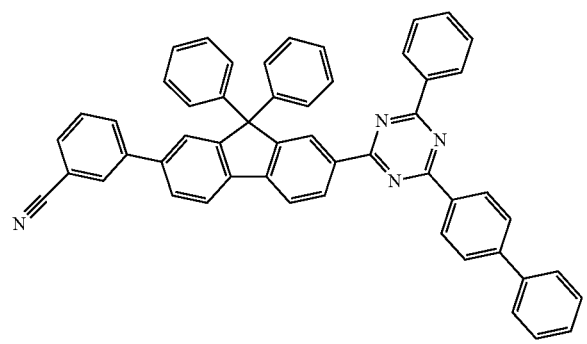
cpd 38
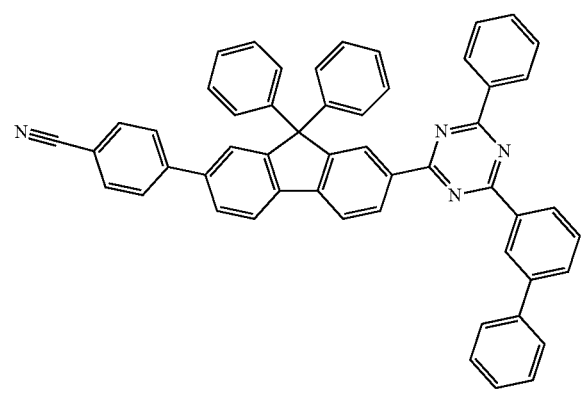
cpd 39
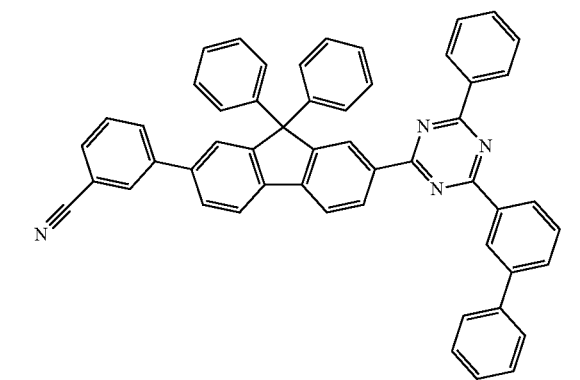
cpd 40
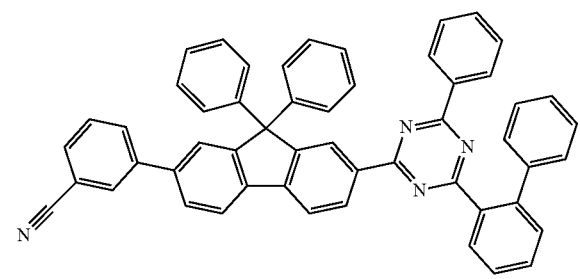
cpd 41
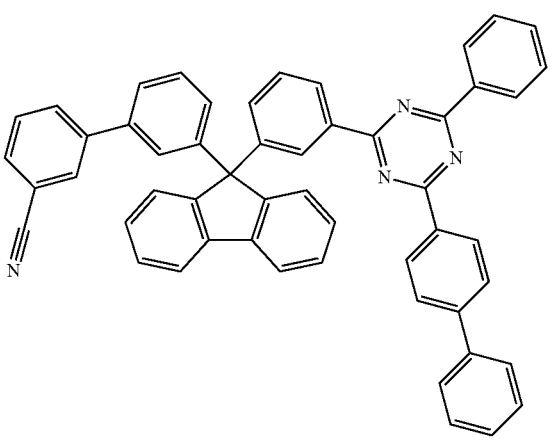
cpd 42
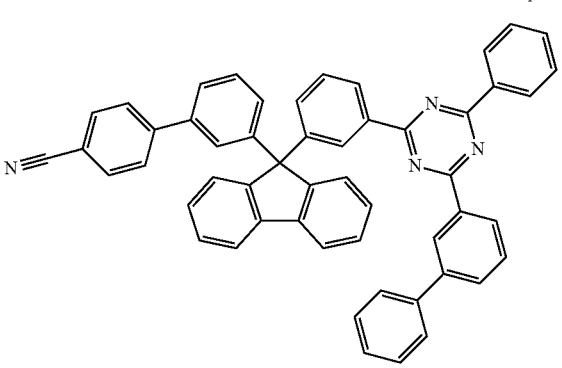
cpd 43
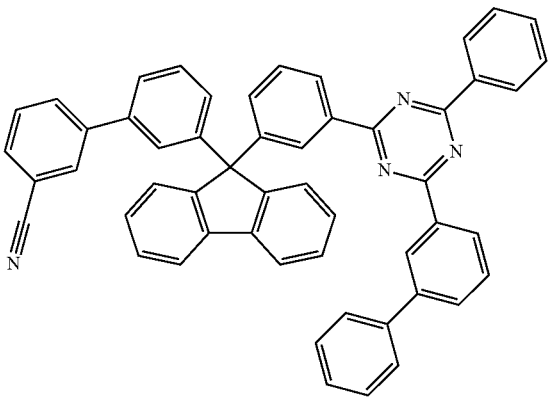
cpd 44
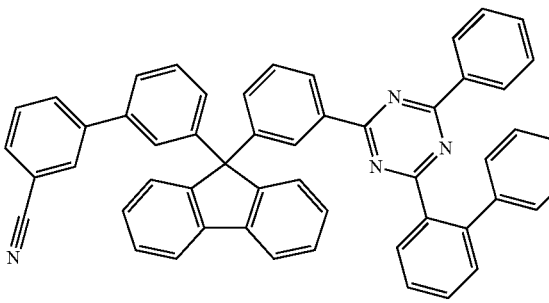

-continued
cpd 45
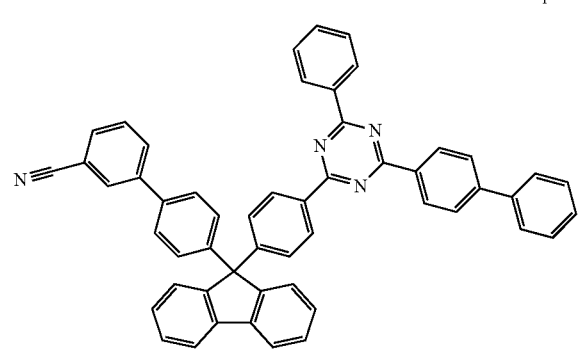
cpd 46
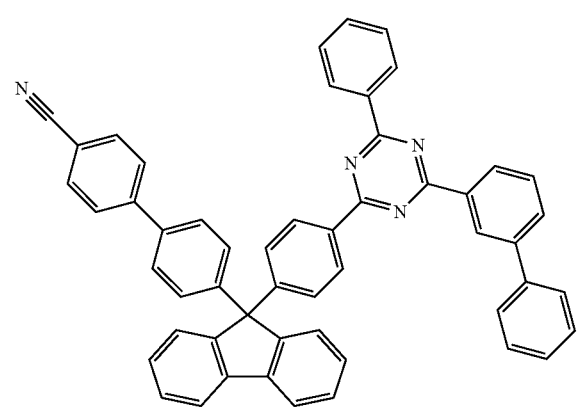
cpd 47
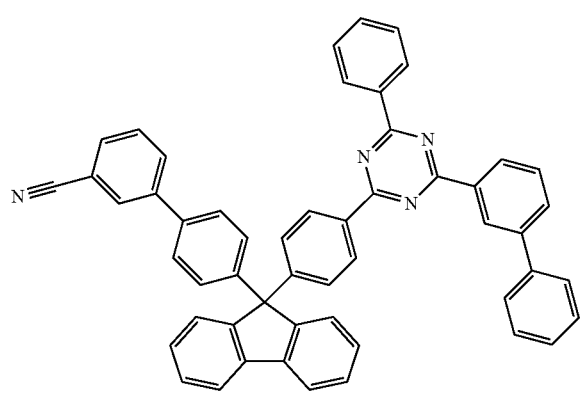
cpd 48
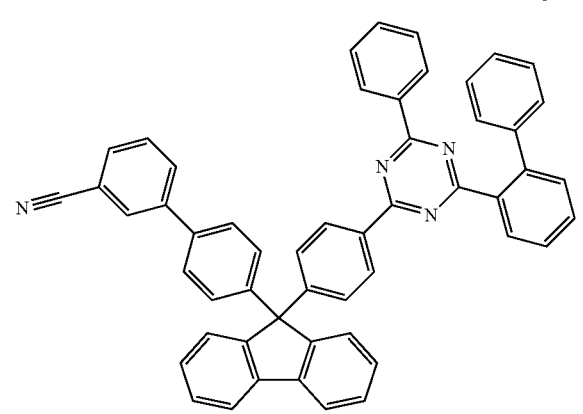
-continued
cpd 49
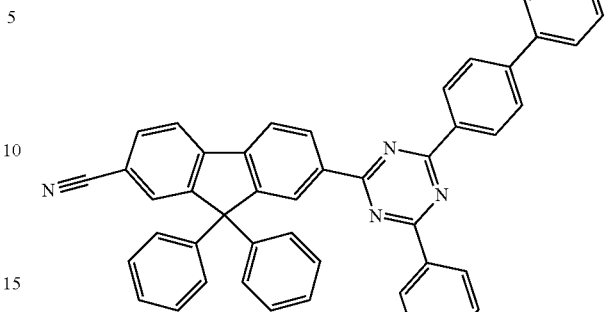
cpd 50
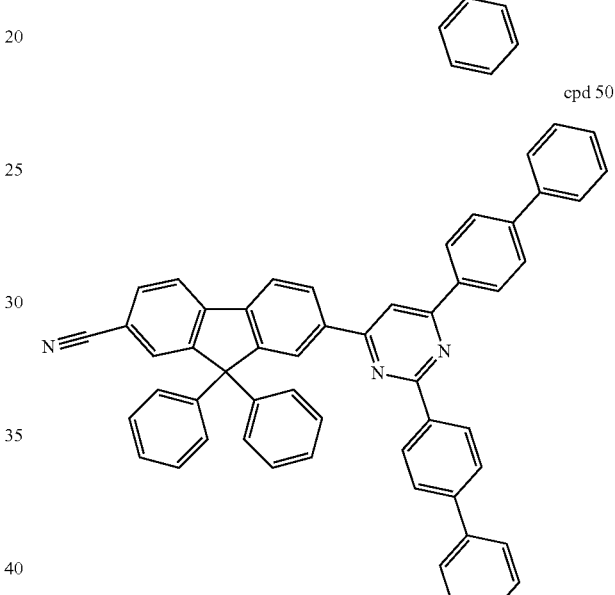
cpd 51
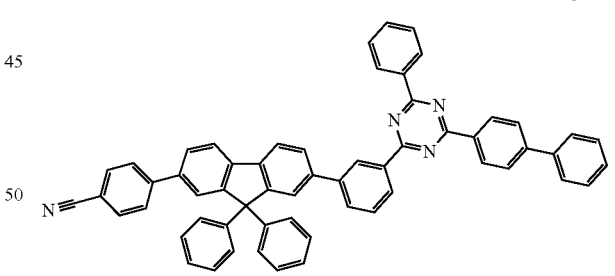
cpd 52
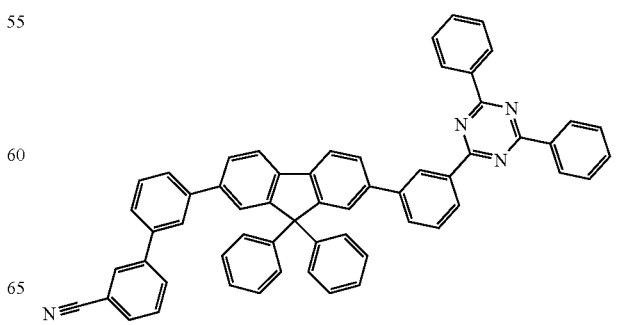

cpd 53
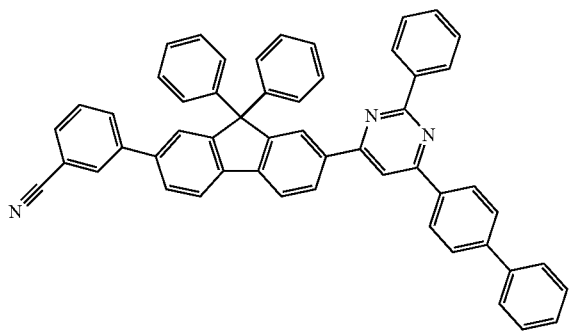
cpd 54
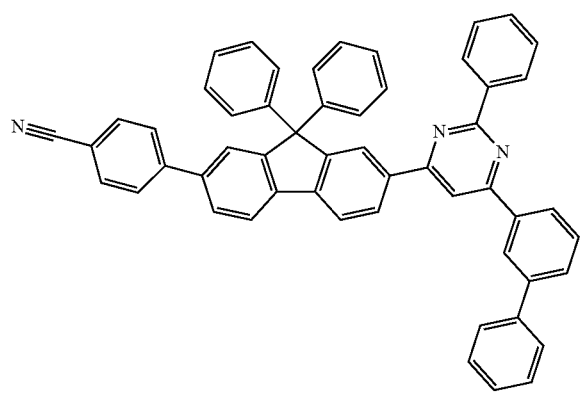
cpd 55
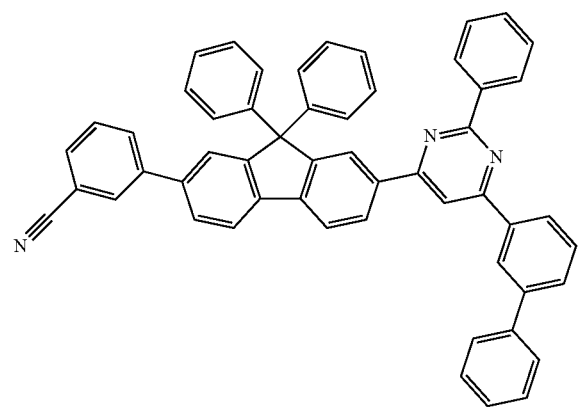
cpd 56
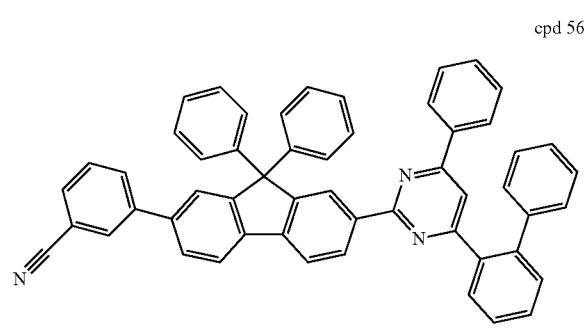
cpd 57
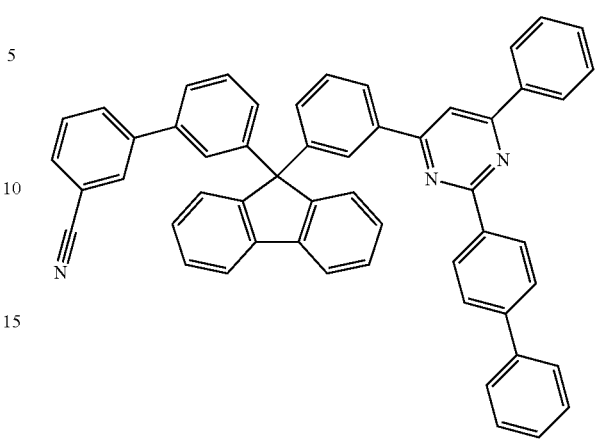
cpd 58
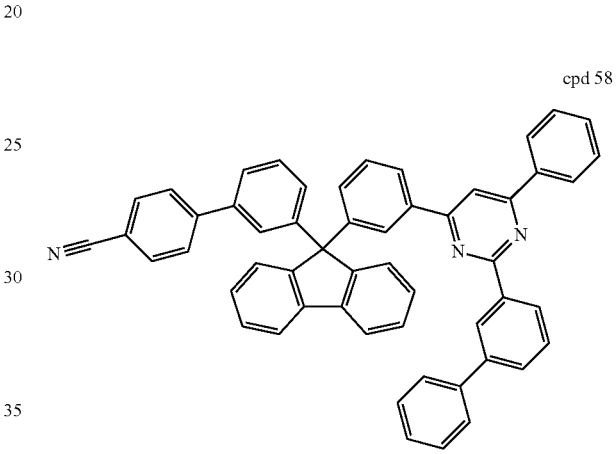
cpd 59
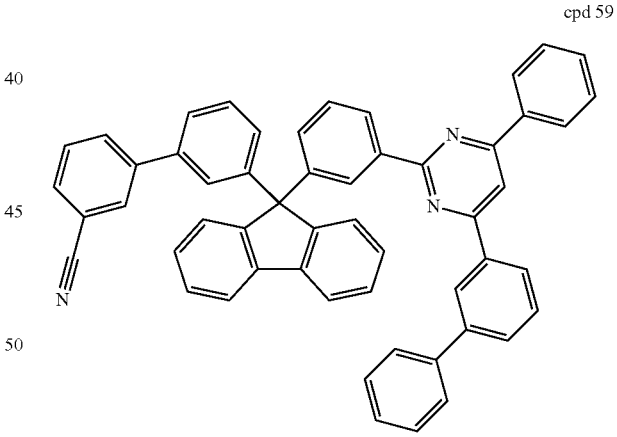
cpd 60
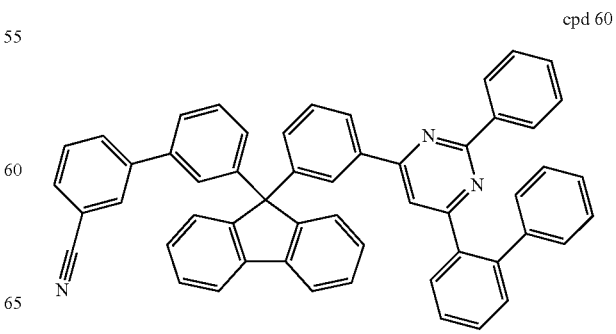

cpd 61
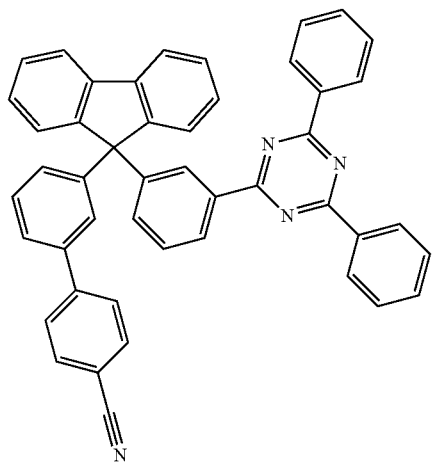
cpd 64
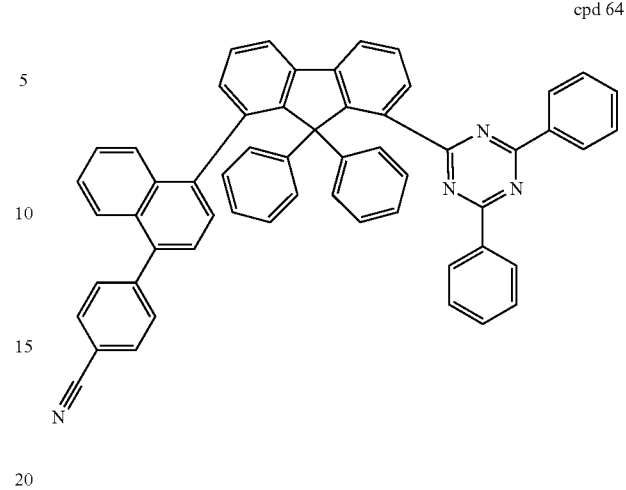
cpd 62
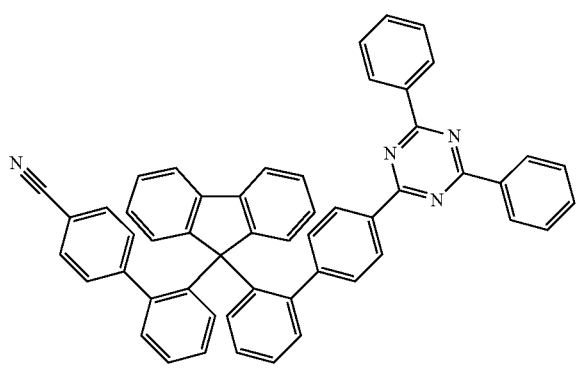
cpd 65
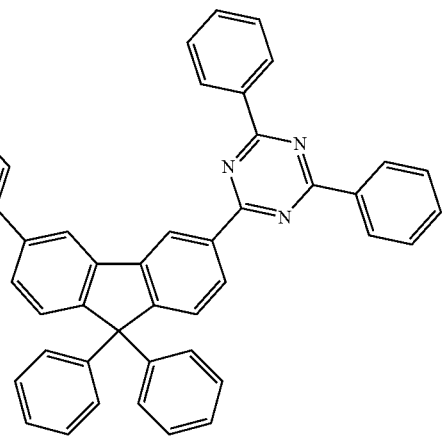
cpd 63
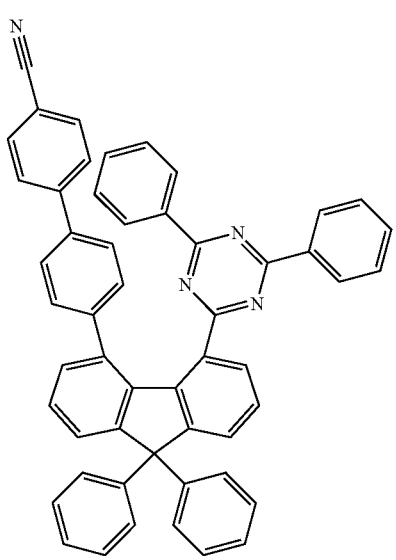
cpd 66
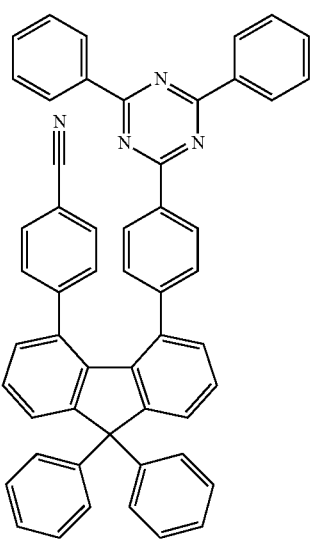

cpd 67
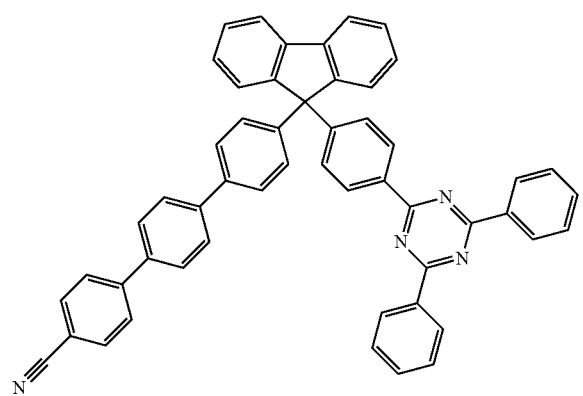
cpd 68
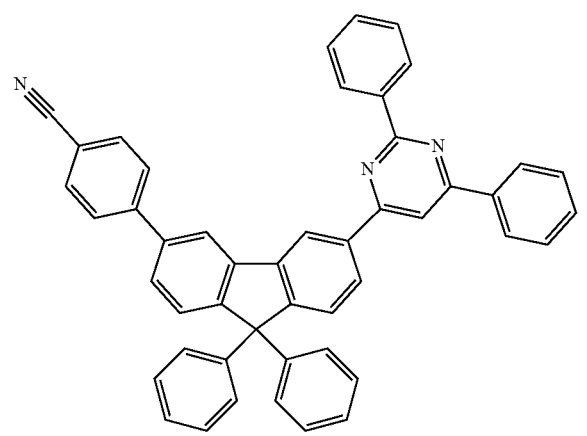
cpd 69
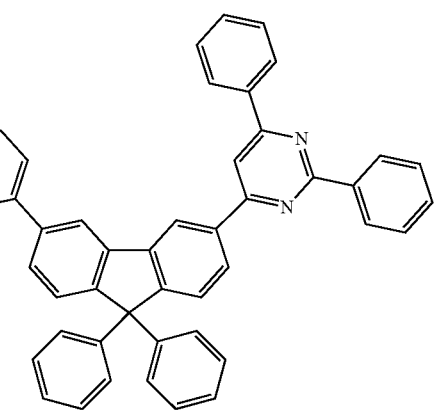
cpd 70
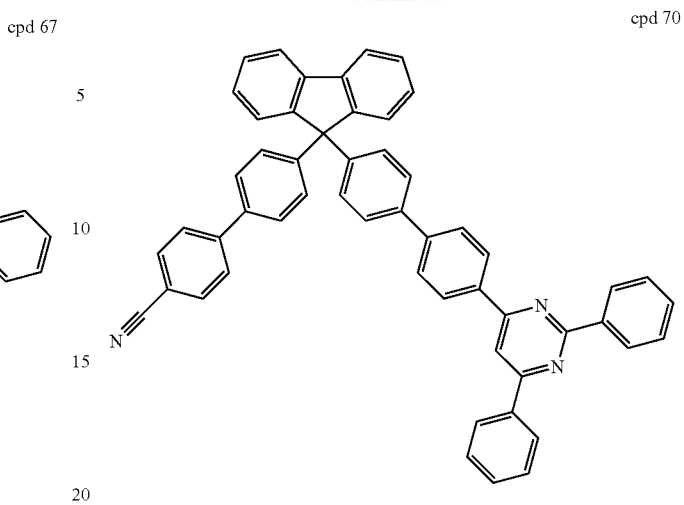
cpd 71
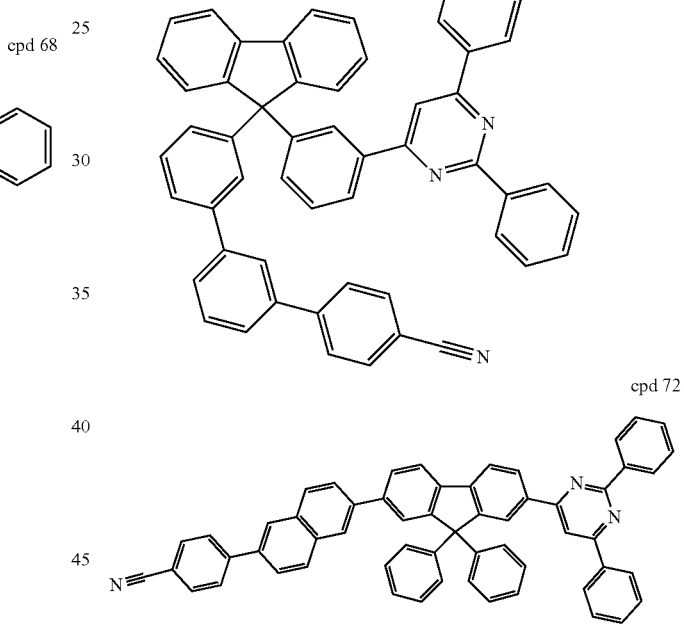
cpd 72
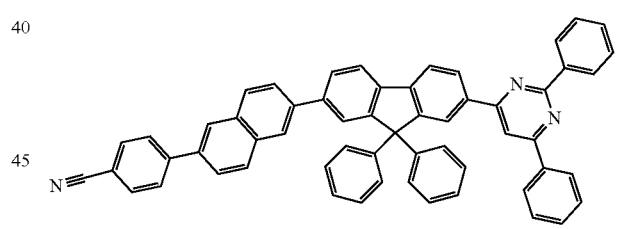
cpd 73 cpd 74
cpd 78
cpd 75
cpd 79
cpd 76
cpd 77
cpd 80
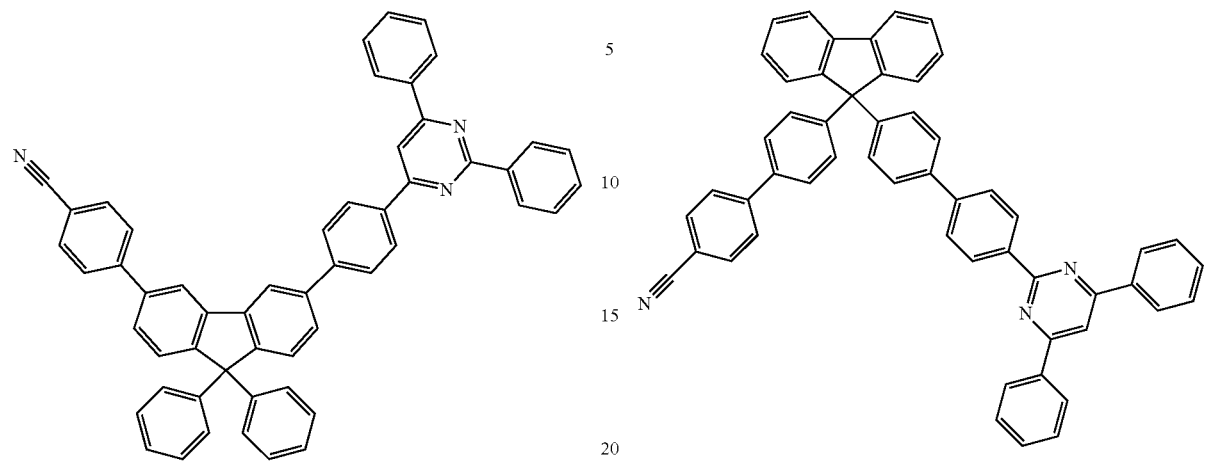
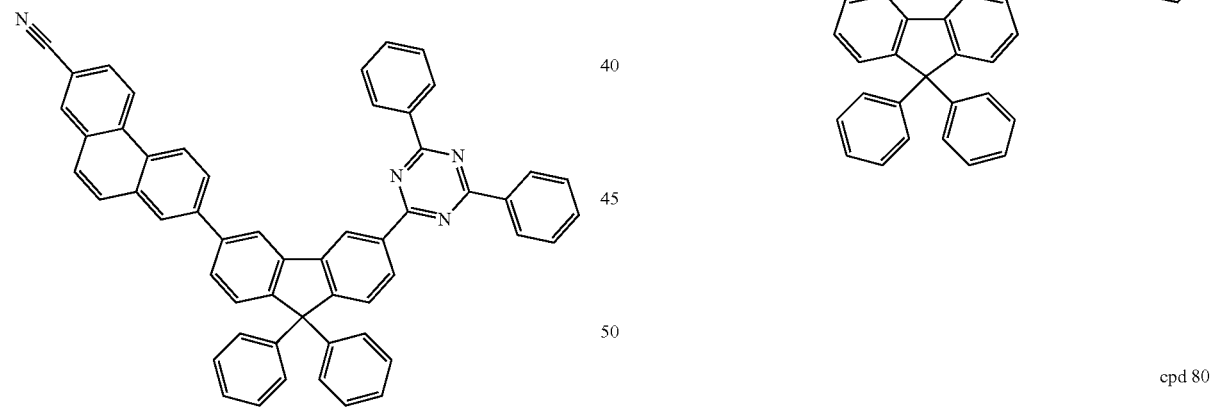
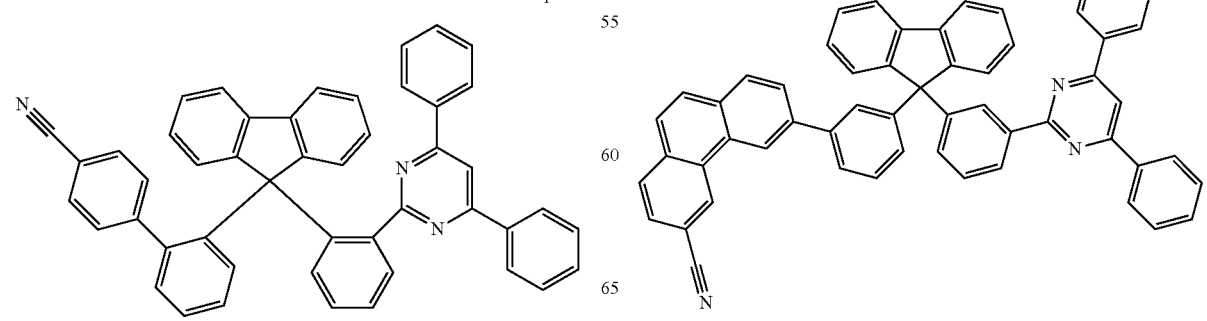

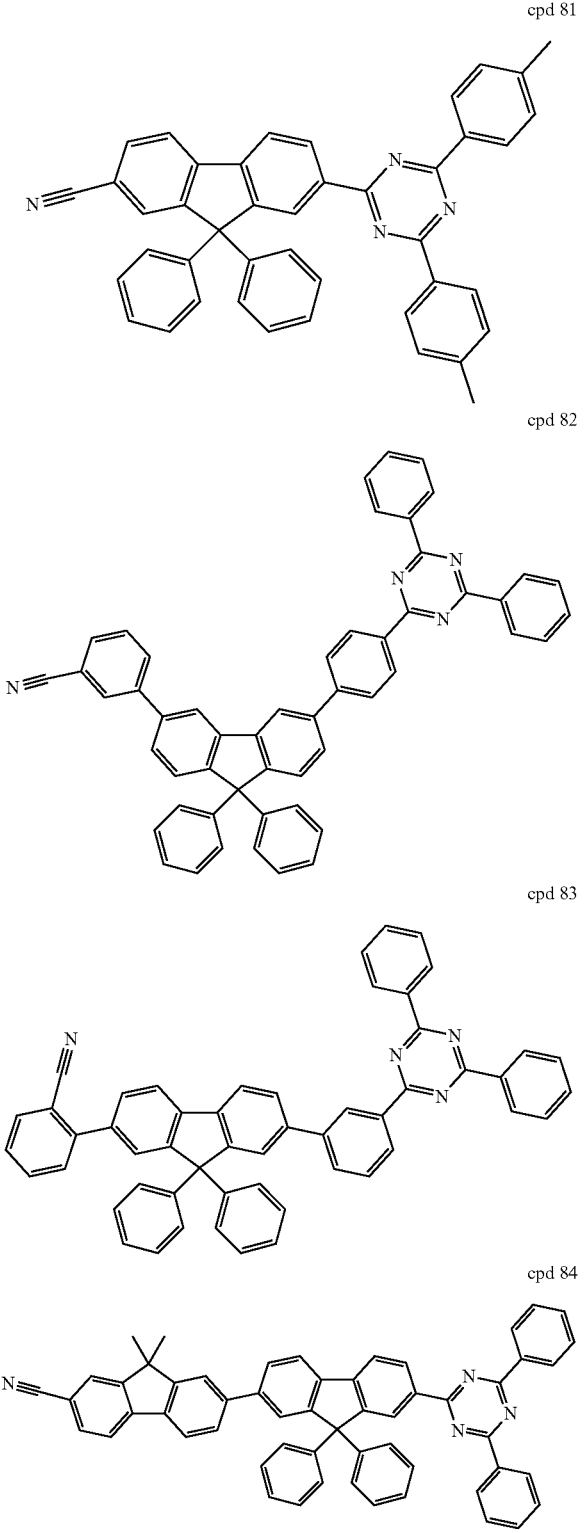

cpd 81
cpd 82
cpd 83
cpd 84

The present specification provides an organic light emitting device including: a first electrode; a second electrode facing the first electrode; and at least one organic material layer interposed between the first electrode and the second electrode, wherein the at least one organic material layer contains the fluorene derivative of Chemical Formula 1.

According to an embodiment of the present specification, the first electrode can be an anode and the second electrode can be a cathode.

According to an embodiment of the present specification, the first electrode can be a cathode and the second electrode can be an anode.

The organic light emitting device according to the present specification can be manufactured by conventional methods and materials for manufacturing organic light emitting devices, except that the one or more organic material layers are formed using the aforementioned compound.

The organic material layer of the organic light emitting device according to the present specification can have a single layer structure, or a multiple layer structure in which two or more organic material layers are laminated.

In an embodiment of the present specification, the organic material layer can include an electron injection layer, an electron transport layer, or an electron injection and transport layer, and the electron injection layer, the electron transport layer, or the electron injection and transport layer can contain the fluorene derivative of Chemical Formula 1.

In an embodiment of the present specification, the organic material layer can include an electron control layer and the electron control layer can include the fluorene derivative of Chemical Formula 1.

In an embodiment of the present specification, the organic material layer can include a hole injection layer or a hole transport layer, and the hole injection layer or the hole transport layer can contain the fluorene derivative of Chemical Formula 1.

In an embodiment of the present specification, the organic material layer can include a hole control layer and the hole control layer can contain the fluorene derivative of Chemical Formula 1.

In an embodiment of the present specification, the organic material layer can include a light emitting layer and the light emitting layer can include the fluorene derivative of Chemical Formula 1.

According to an embodiment of the present specification, the organic material layer can be formed using the fluorene derivative of Chemical Formula 1 in combination with LiQ.

According to an embodiment of the present specification, the organic material layer can be formed using the fluorene derivative of Chemical Formula 1 in combination with LiQ, and a different electron transport layer material can be used at the front or back of the organic material layer formed using the combination of the fluorene derivative of Chemical Formula 1 and LiQ.

According to an embodiment of the present specification, the electron injection layer, the electron transport layer, or the electron injection and transport layer can be formed using a combination of the compound of Chemical Formula 1 and LiQ in a weight ratio of 3:7 to 7:3.

For example, the structure of the organic light emitting device according to the present specification can be the same as shown in FIG. 1, but is not limited thereto.

FIG. 1 illustrates an exemplary structure of an organic light emitting device in which a first electrode 2, an organic material layer 3 and a second electrode 4 are laminated on a substrate 1 in the stated order.

FIG. 2 illustrates an exemplary structure of an organic light emitting device in which a first electrode 2, an organic material layer 3, a light emitting layer 5, an electron injection and transport layer 6 and a second electrode 4 are laminated on a substrate 1 in the stated order.

For example, the organic light emitting device according to the present invention can be manufactured by depositing a metal or a metal oxide having conductivity or an alloy thereof on a substrate using a physical vapor deposition (PVD) method such as sputtering or e-beam evaporation to form an anode, forming, on the anode, an organic material layer including a hole injection layer, a hole transport layer, a light emitting layer and an electron transport layer, and an organic material layer containing the fluorene derivative of Chemical Formula 1, and then depositing a material useful for a cathode thereon. Apart from such a method, the organic light emitting device can also be manufactured by sequentially depositing a cathode material, an organic material layer material, and an anode material on the substrate.

Generally, the first electrode material is preferably a material that has a high work function to facilitate injection of holes into the organic material layer. Specifically, examples of the first electrode material that can be used in the present include, but are not limited to: metals such as vanadium, chromium, copper, zinc and gold, and alloys thereof; metal oxides, such as zinc oxide, indium oxide, indium tin oxide (ITO) and indium zinc oxide (IZO); combinations of a metal with metal oxide such as ZnO:Al and $SnO_2$:Sb; conductive polymers such as poly[3,4-(ethylene-1,2-dioxy)thiophene] (PEDT), polypyrrole and polyaniline, and the like.

Generally, the second electrode material is preferably a material that has a low work function to facilitate injection of electrons into the organic material layer. Specific examples of the second electrode material include, but are not limited to metals such as magnesium, calcium, sodium, potassium, titanium, indium, yttrium, lithium, gadolinium, aluminum, silver, tin and lead, and alloys thereof, and multilayered-structure materials such as LiF/Al and $LiO_2$/Al, and the like.

Preferably, the hole injection material is a material favorably receiving holes from the anode at a low voltage, which has a highest occupied molecular orbital (HOMO) between the work function of the anode material and the HOMO of the adjacent organic material layer. Specifically, examples of the hole injection material include, but are not limited to, metal-porphyrin, oligothiophene, arylamine-based organic substances, hexanitrile-hexaazatriphenylene-based organic substances, quinacridone-based organic substances, perylene-based organic substances, anthraquinone, polyaniline and polycompound-based conductive polymers, and the like.

The hole transport material is a material that is capable of receiving holes from the anode or the hole injection layer and transporting the holes to the light emitting layer and is preferably a material having a high hole mobility. Specifically, examples of the hole transport material include, but are not limited to, arylamine-based compounds, conductive polymers, block copolymers having both a conjugated moiety and a non-conjugated moiety, and the like.

The light emitting material is a material that is capable of receiving holes and electrons from the hole transport layer and the electron transport layer, respectively, and emitting visible light using an energy of excitons generated by recombination between the holes and electrons, and is preferably a material having excellent quantum efficiency for fluorescence or phosphorescence. Specifically, examples of the light emitting material include, but are not limited to: 8-hydroxy-quinoline aluminum complexes ($Alq_3$); carbazole-based compounds; dimerized styryl compounds; BAlq; 10-hydroxybenzoquinoline-metal compounds; benzoxazole-, benzthiazole- and benzimidazole-based compounds; poly(p-phenylenevinylene) (PPV)-based polymers; spiro compounds; polyfluorene, rubrene; and the like.

The method for preparing a fluorene derivative and the method for manufacturing an organic light emitting device including the same will be described in detail with reference to the following Preparation Examples and Examples. However, the following Preparation Examples and Examples are provided only for illustration of the present specification and should not be construed as limiting the scope of the present specification.

EXAMPLES

Preparation Example

Preparation Example 1: Preparation of Compound 1

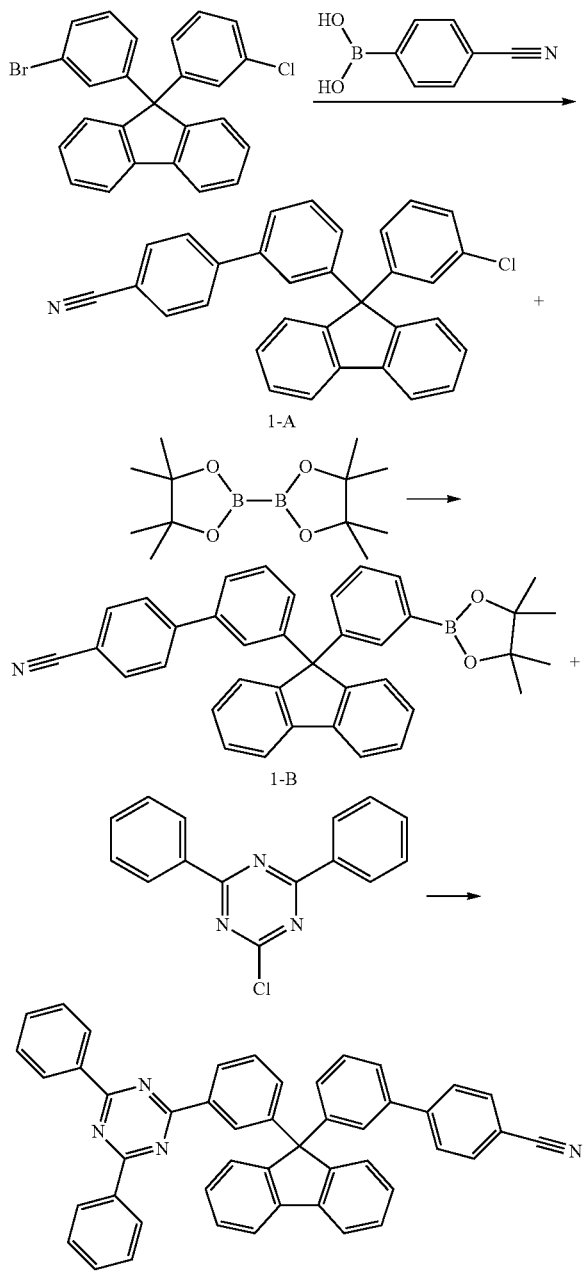

Under a nitrogen atmosphere, the 9-(3-bromophenyl)-9-(3-chlorophenyl)-9H-fluorene (20 g, 46.3 mmol), (4-cyanophenyl)-boronic acid (6.8 g, 46.3 mmol) and potassium carbonate (12.8 g, 92.6 mmol) were stirred under heating in tetrahydrofuran (THF) (200 mL). Tetrakis(triphenylphosphine)palladium (0) (1.6 g, 1.39 mmol) was added to the resulting reaction solution, followed by further stirring under heating for 2 hours. The reaction solution was allowed to cool to room temperature and ethanol slurry purification was conducted to prepare Compound 1-A (20 g, yield 95%) shown above.

MS: [M+H]$^+$=454

Under a nitrogen atmosphere, the aforementioned Compound 1-A (21 g, 44.1 mmol), bis(pinacolato)diboron (12.3 g, 48.5 mmol) and potassium acetate (8.6 g, 88.2 mmol) were stirred under heating in dioxane (200 mL). Bis(dibenzylideneacetone)palladium (0) (0.76 g, 1.32 mmol) and triphenylphosphine (0.74 g, 2.64 mmol) were added to the resulting reaction solution, followed by further stirring under heating for 4 hours. The reaction solution was allowed to cool to room temperature, and ethanol slurry purification was conducted to prepare Compound 1-B (28 g, yield 94%) shown above.

MS: [M+H]$^+$=546

Under a nitrogen atmosphere, Compound 1-B (28 g, 41.4 mmol), 2-chloro-4,6-diphenyl-1,3,5-triazine (11.1 g, 41.4 mmol) and potassium carbonate (11.4 g, 82.8 mmol) were stirred under heating in tetrahydrofuran (THF) (200 mL). Tetrakis(triphenylphosphine)-palladium (0) (1.44 g, 1.24 mmol) was added to the resulting reaction solution, followed by further stirring under heating for 3 hours. The reaction solution was allowed to cool to room temperature, and ethanol slurry purification was conducted to prepare Compound 1 (25 g, yield 93%) shown above.

MS: [M+H]$^+$=651

Preparation Example 2: Preparation of Compound 2

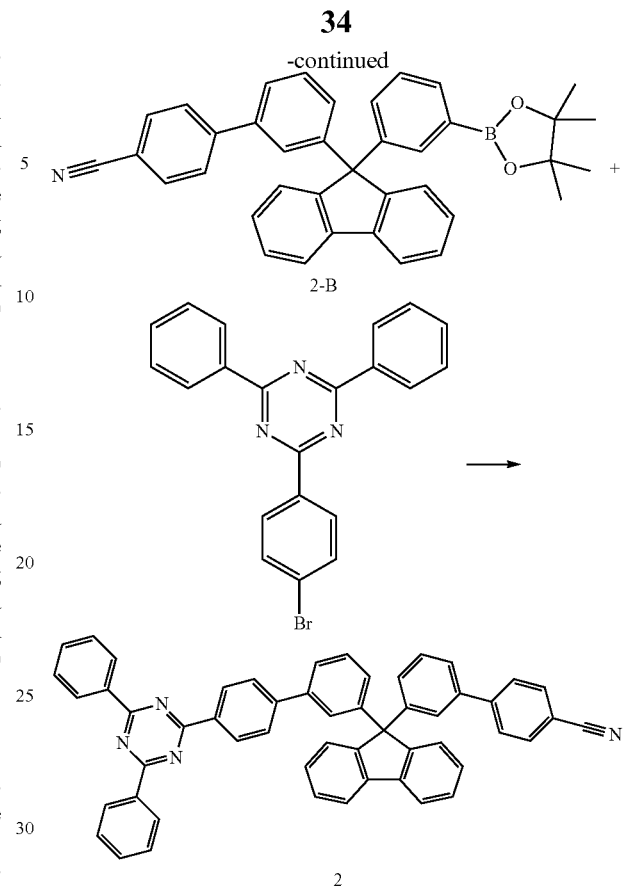

Compound 2 shown above was prepared in the same manner as in preparation of Compound 1, except that 2-(4-bromophenyl)-4,6-diphenyl-1,3,5-triazine was used instead of 2-chloro-4,6-diphenyl-1,3,5-triazine.

MS: [M+H]$^+$=727

Preparation Example 3: Preparation of Compound 5

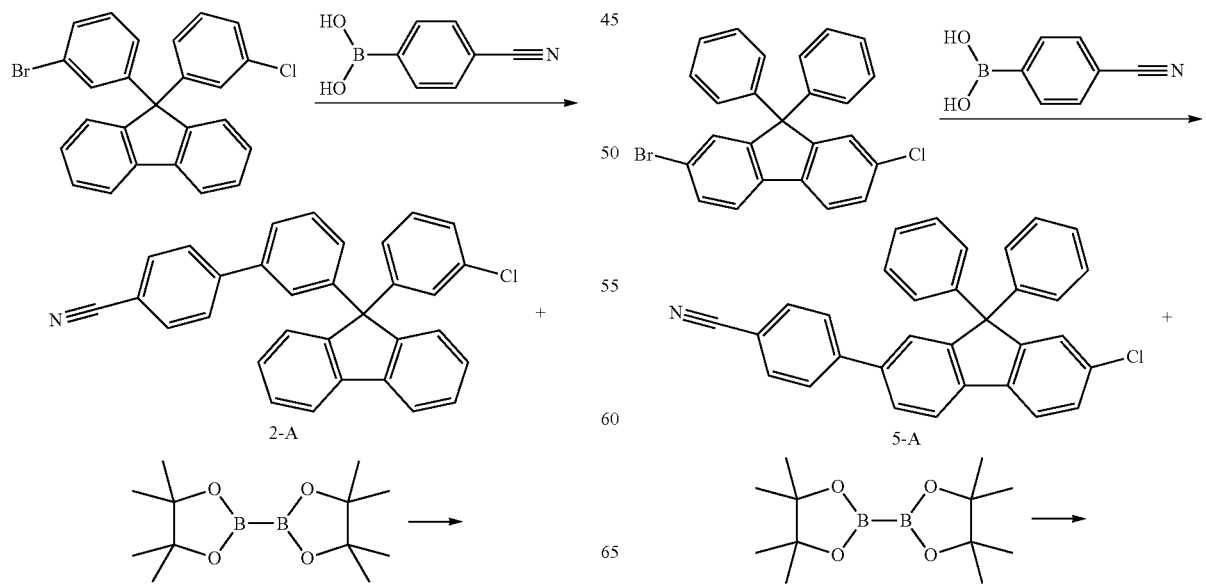

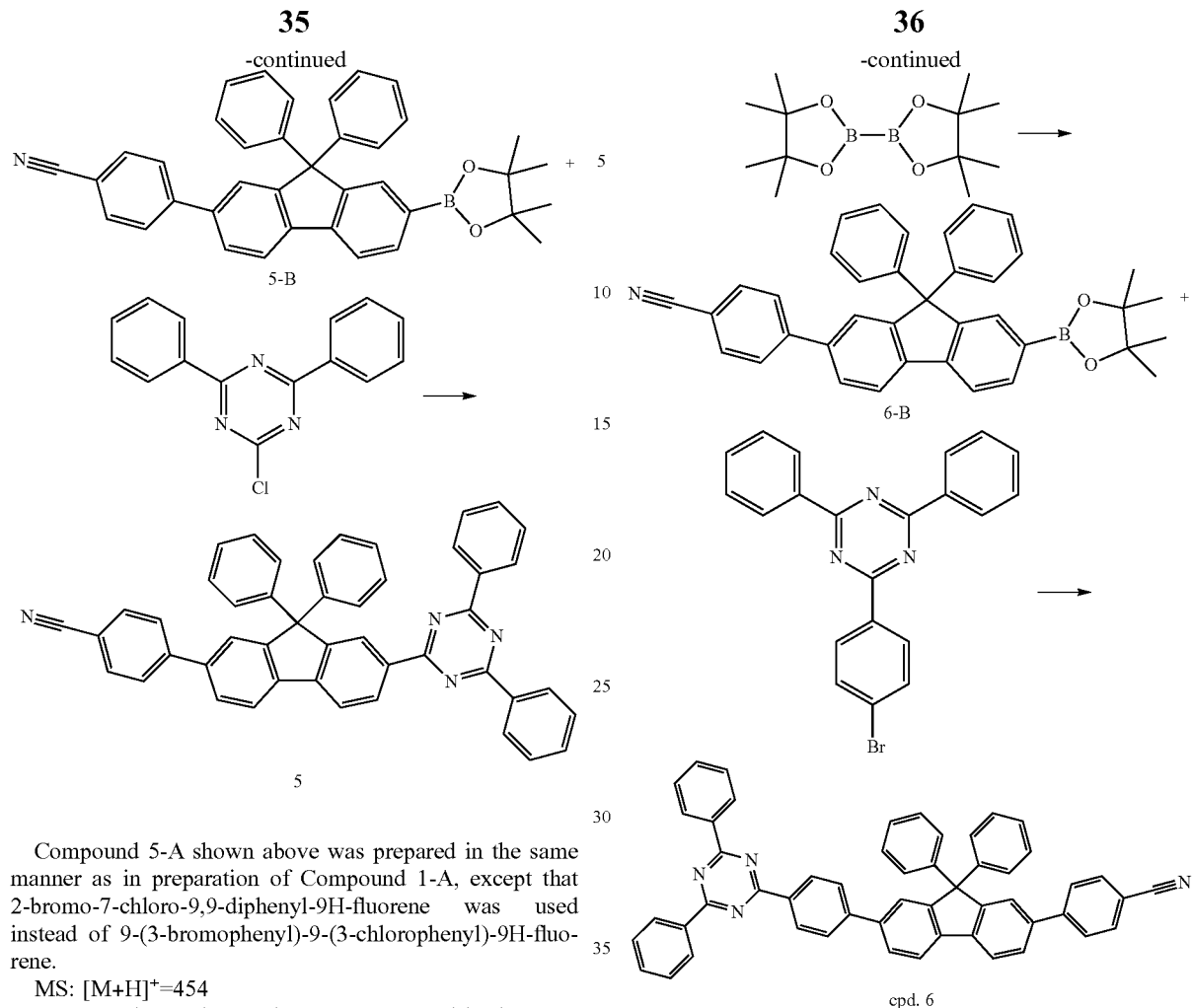

Compound 5-A shown above was prepared in the same manner as in preparation of Compound 1-A, except that 2-bromo-7-chloro-9,9-diphenyl-9H-fluorene was used instead of 9-(3-bromophenyl)-9-(3-chlorophenyl)-9H-fluorene.

MS: [M+H]$^+$=454

Compound 5-B shown above was prepared in the same manner as in preparation of Compound 1-B, except that Compound 5-A was used instead of Compound 1-A.

MS: [M+H]$^+$=546

Compound 5 shown above was prepared in the same manner as in preparation of Compound 1, except that Compound 5-B was used instead of Compound 1-B.

MS: [M+H]$^+$=651

Preparation Example 4: Preparation of Compound 6

Compound 6 shown above was prepared in the same manner as in preparation of Compound 5, except that 2-(4-bromophenyl)-4,6-diphenyl-1,3,5-triazine was used instead of 2-chloro-4,6-diphenyl-1,3,5-triazine.

MS: [M+H]$^+$=727

Preparation Example 5: Preparation of Compound 13

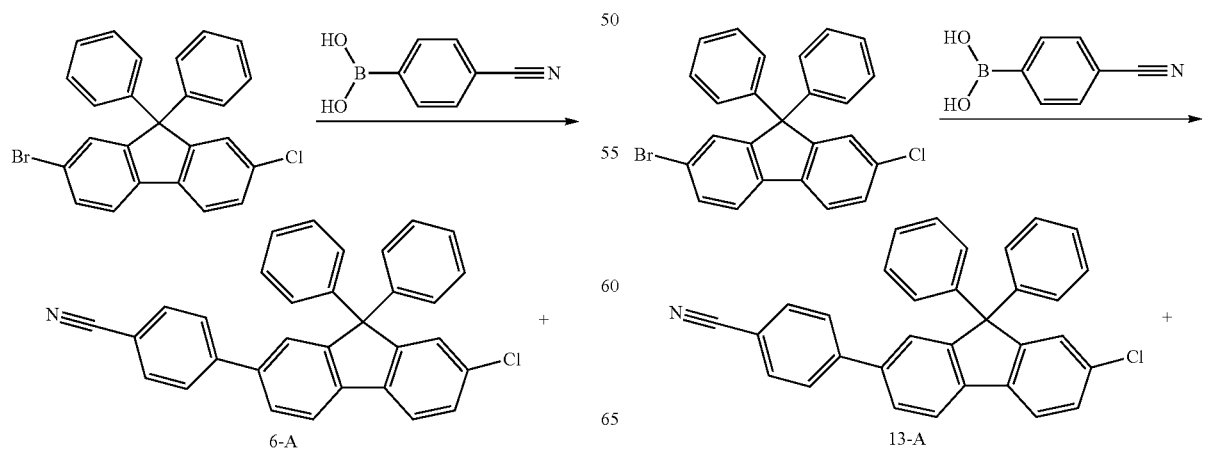

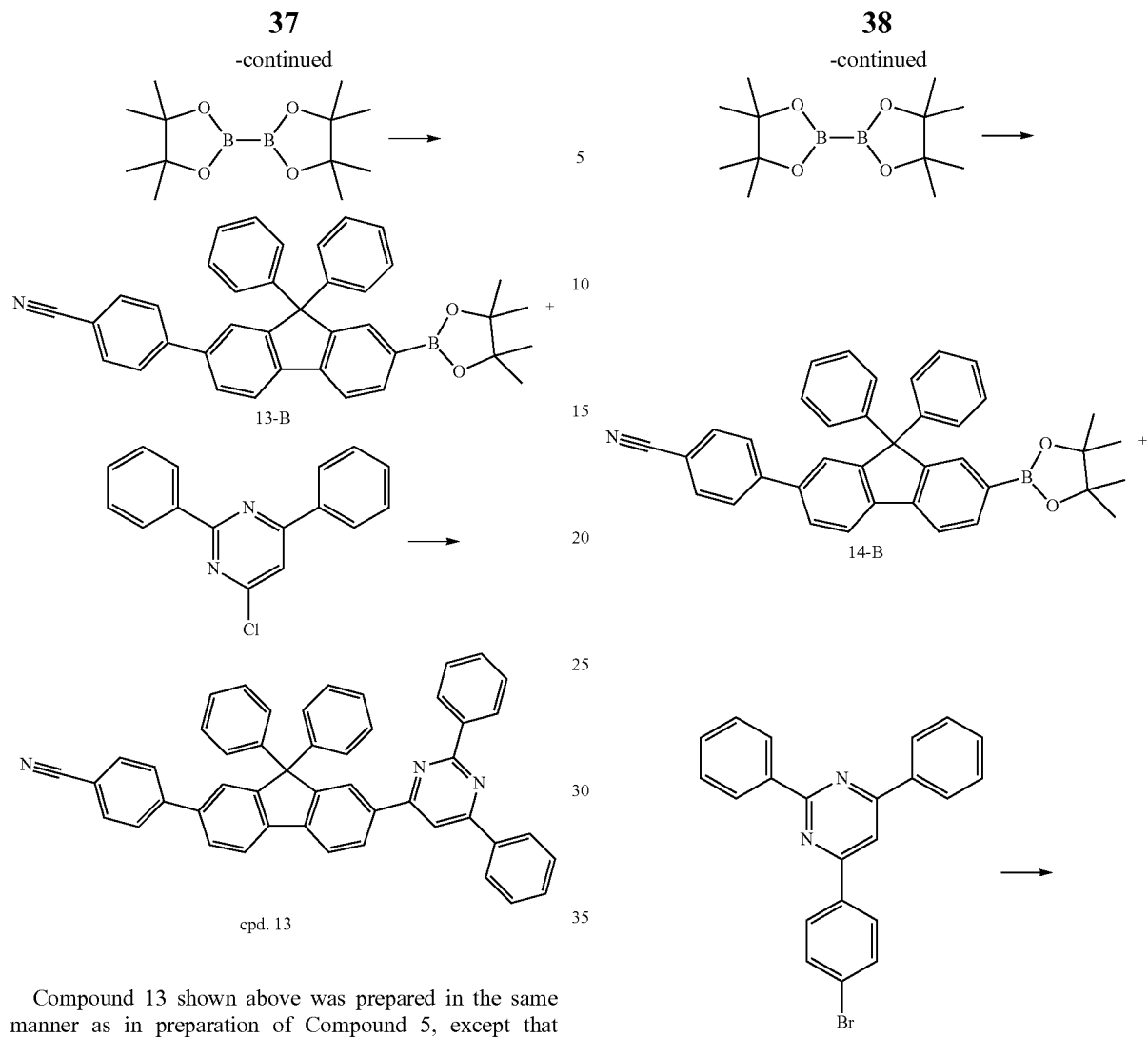

Compound 13 shown above was prepared in the same manner as in preparation of Compound 5, except that 4-chloro-2,6-diphenylpyrimidine was used instead of 2-chloro-4,6-diphenyl-1,3,5-triazine.

MS: [M+H]$^+$=650

Preparation Example 6: Preparation of Compound 14

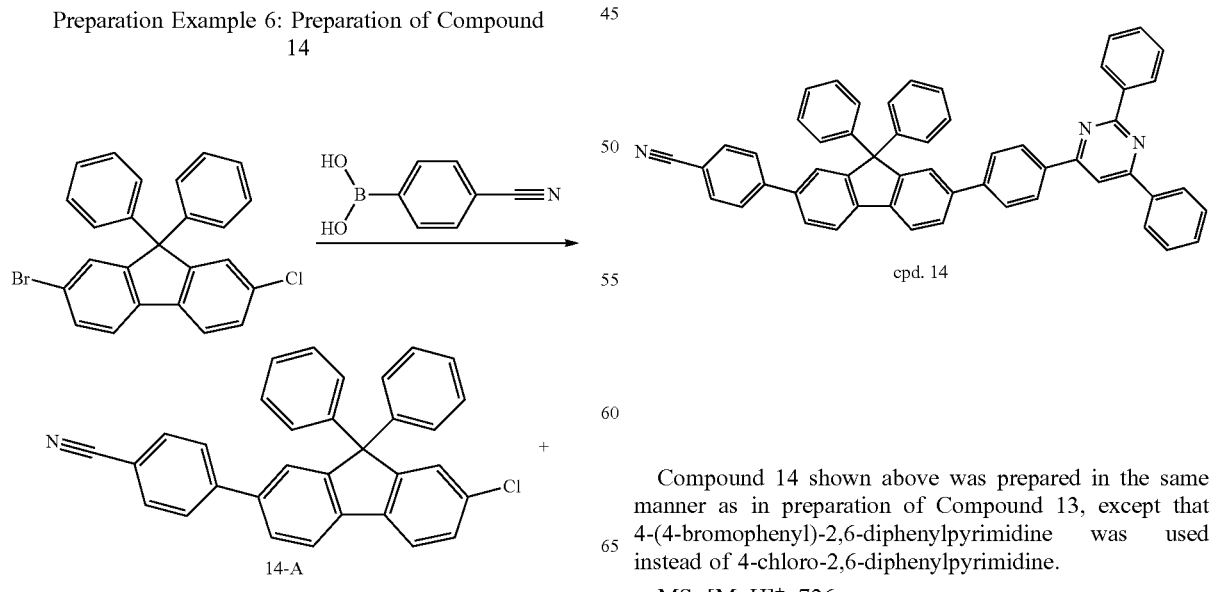

Compound 14 shown above was prepared in the same manner as in preparation of Compound 13, except that 4-(4-bromophenyl)-2,6-diphenylpyrimidine was used instead of 4-chloro-2,6-diphenylpyrimidine.

MS: [M+H]$^+$=726

Preparation Example 7: Preparation of Compound 20
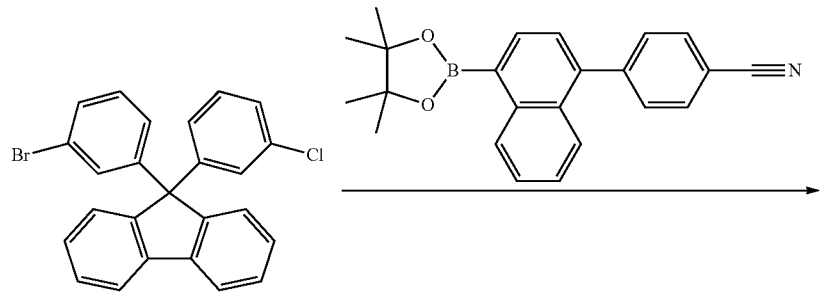
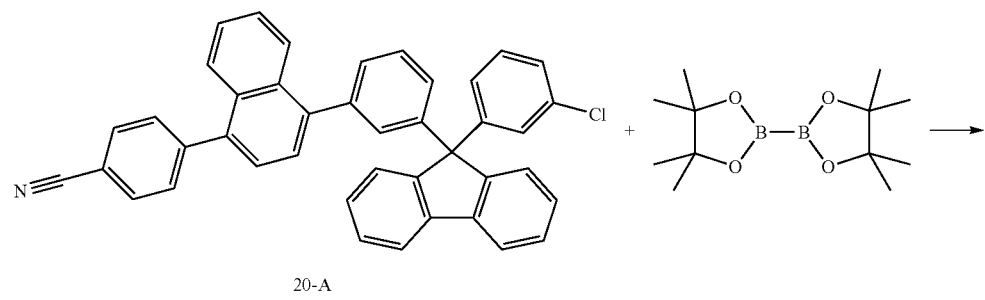
20-A
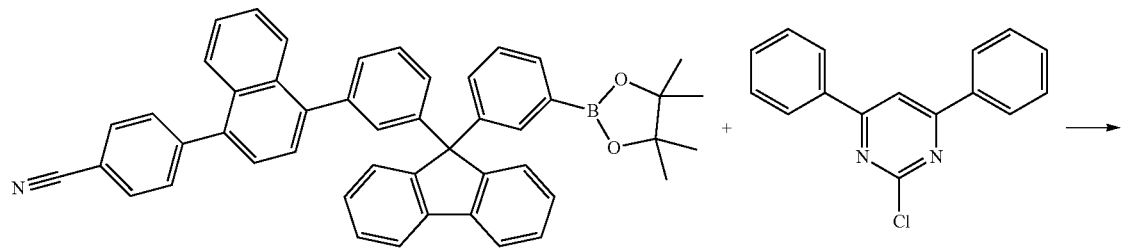
20-B
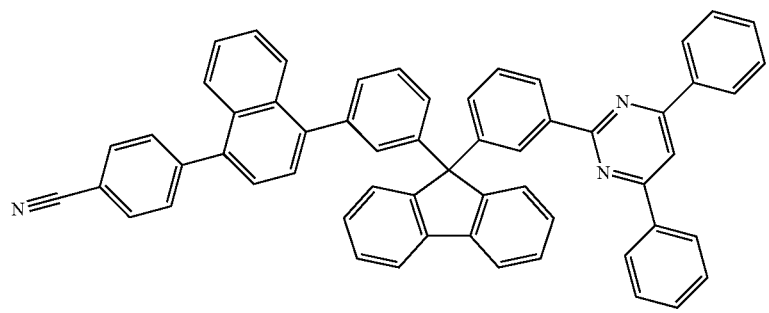
cpd. 20

Compound 20-A shown above was prepared in the same manner as in preparation of Compound 1-A, except that 4-(4-(4,4,5,5-tetramethyl-1,3,2-dioxaborolan-2-yl)naphthalen-1-yl)benzonitrile was used instead of (4-cyanophenyl)boronic acid.

MS: [M+H]$^+$=580

Compound 20-B shown above was prepared in the same manner as in preparation of Compound 1-B, except that Compound 20-A was used instead of Compound 1-A.

MS: [M+H]$^+$=672

Compound 20 shown above was prepared in the same manner as in preparation of Compound 1, except that Compound 20-B was used instead of Compound 1-B.

MS: [M+H]$^+$=776

Preparation Example 8: Preparation of Compound 25

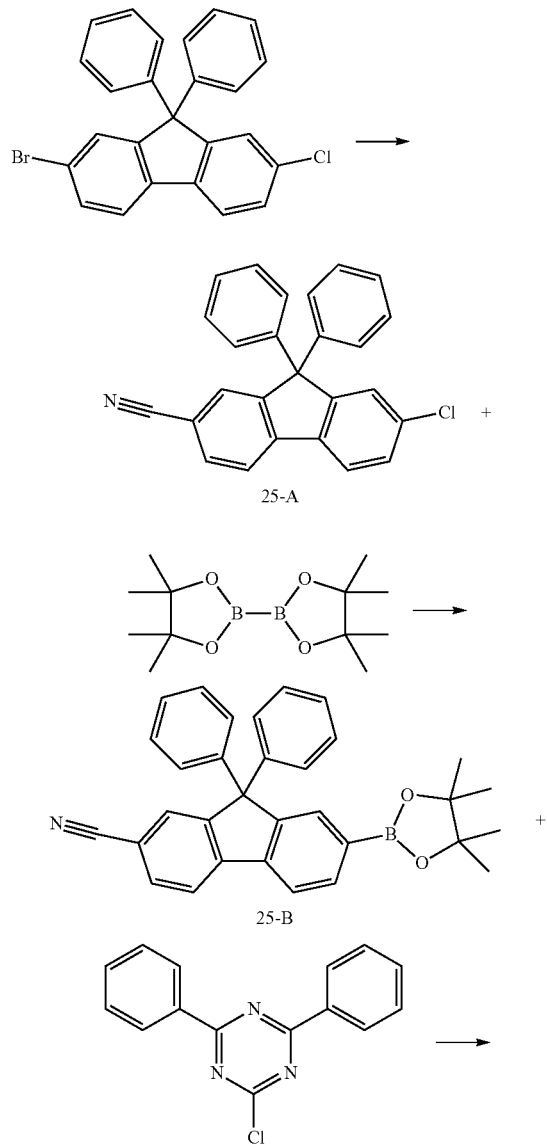

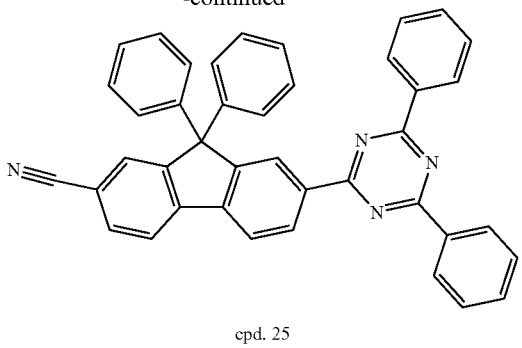

cpd. 25

Under a nitrogen atmosphere, the aforementioned 9-(3-bromophenyl)-9-(3-chlorophenyl)-9H-fluorene (20 g, 46.3 mmol) and Zn(CN)$_2$ (2.77 g, 23.6 mmol) were stirred under heating in dimethylacetamide (200 mL). Tetrakis(triphenylphosphine)palladium (0) (2.68 g, 2.32 mmol) was added to the resulting reaction solution, followed by further stirring under heating for 1 hour. The reaction solution was allowed to cool to room temperature and ethanol slurry purification was conducted to prepare Compound 25-A (16 g, yield 91.4%) shown above.

MS: [M+H]$^+$=378

Under a nitrogen atmosphere, Compound 25-A (16 g, 42.3 mmol), bis(pinacolato)diboron (11.8 g, 46.6 mmol) and potassium acetate (9.1 g, 93.2 mmol) were stirred under heating in dioxane (150 mL). Bis(dibenzylideneacetone)palladium (0) (0.80 g, 1.40 mmol) and triphenylphosphine (0.79 g, 2.80 mmol) were added to the resulting reaction solution, followed by further stirring under heating for 2 hours. The reaction solution was allowed to cool to room temperature and ethanol slurry purification was conducted to prepare Compound 25-B (18.5 g, yield 93.4%) shown above.

MS: [M+H]$^+$=470

Under a nitrogen atmosphere, Compound 25-B (18.5 g, 39.4 mmol), 2-chloro-4,6-diphenyl-1,3,5-triazine (10.5 g, 39.4 mmol) and potassium carbonate (8.17 g, 59.1 mmol) were stirred under heating in tetrahydrofuran (THF) (200 mL). Tetrakis(triphenylphosphine)palladium (0) (1.37 g, 1.18 mmol) was added to the resulting reaction solution, followed by further stirring under heating for 2 hours. The reaction solution was allowed to cool to room temperature and ethanol slurry purification was conducted to prepare Compound 25 (21 g, yield 92.7%) shown above.

MS: [M+H]$^+$=575

Preparation Example 9: Preparation of Compound 27

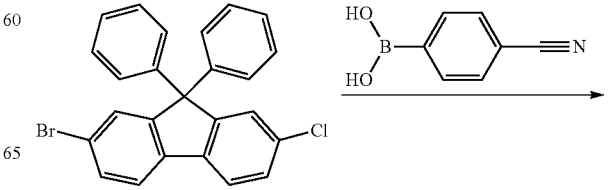

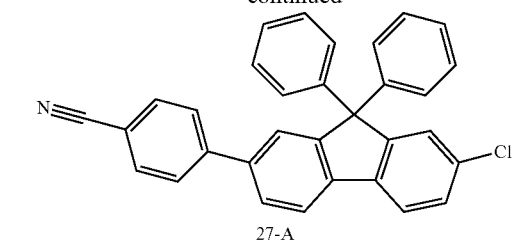
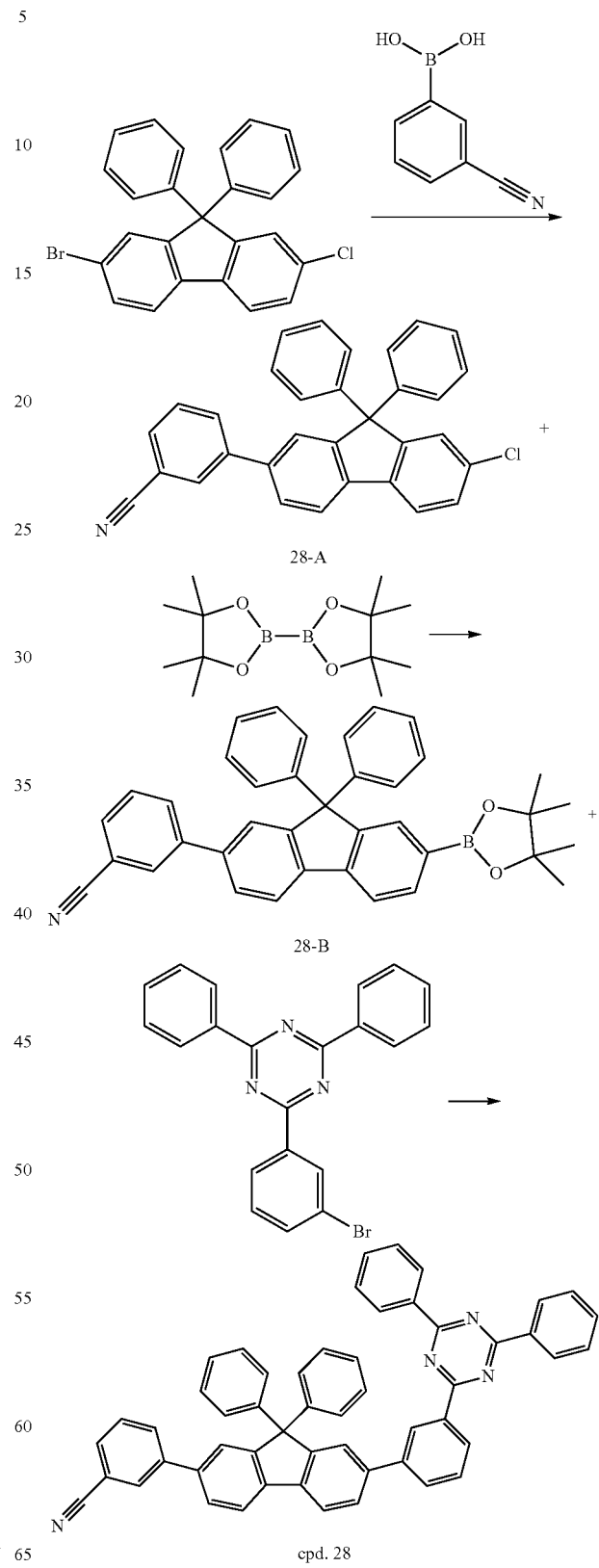
Compound 27 shown above was prepared in the same manner as in preparation of Compound 5, except that 2-(3-bromophenyl)-4,6-diphenyl-1,3,5-triazine was used instead of 2-chloro-4,6-diphenyl-1,3,5-triazine.
MS: $[M+H]^+$=727
Preparation Example 10: Preparation of Compound 28

Compound 28-A shown above was prepared in the same manner as in preparation of Compound 27-A, except that (3-cyanophenyl)boronic acid was used instead of (4-cyanophenyl)boronic acid.

MS: [M+H]$^+$=454

Compound 28-B shown above was prepared in the same manner as in preparation of Compound 27-B, except that Compound 28-A was used instead of Compound 27-A.

MS: [M+H]$^+$=546

Compound 28 shown above was prepared in the same manner as in preparation of Compound 27, except that Compound 28-B was used instead of Compound 27-B.

MS: [M+H]$^+$=727

Preparation Example 11: Preparation of Compound 37

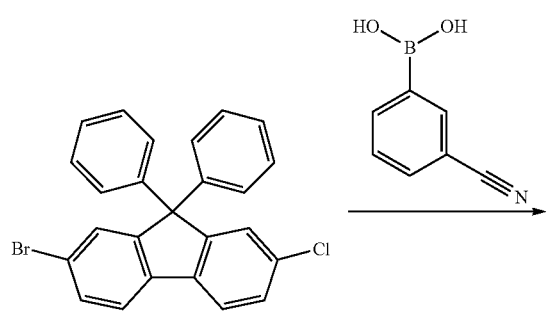

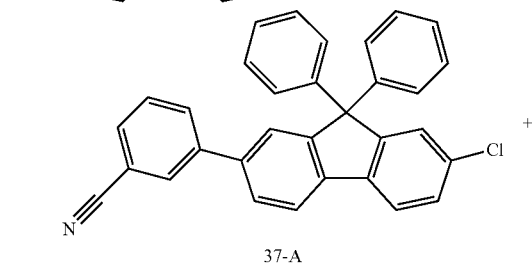

37-A

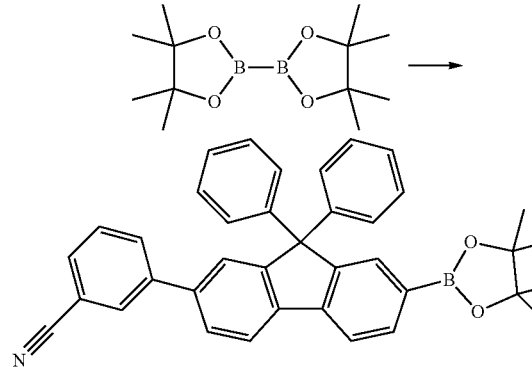

37-B

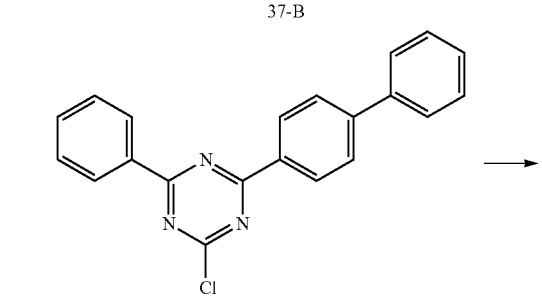

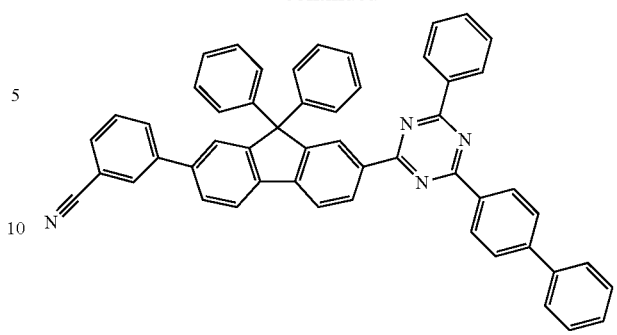

cpd. 37

Compound 37 shown above was prepared in the same manner as in preparation of Compound 28, except that 2-([1,1'-biphenyl]-4-yl)-4-chloro-6-phenyl-1,3,5-triazine was used instead of 2-(3-bromophenyl)-4,6-diphenyl-1,3,5-triazine.

MS: [M+H]$^+$=727

Preparation Example 12: Preparation of Compound 46

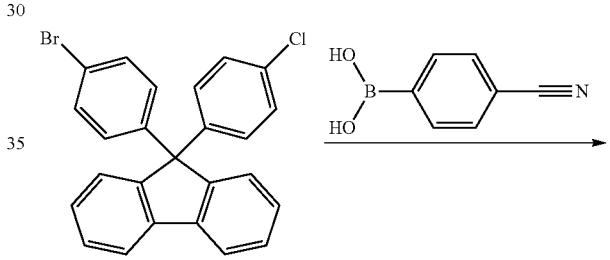

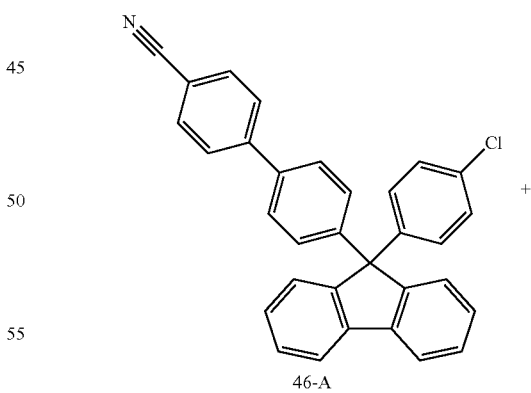

46-A

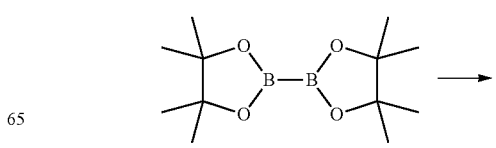

47

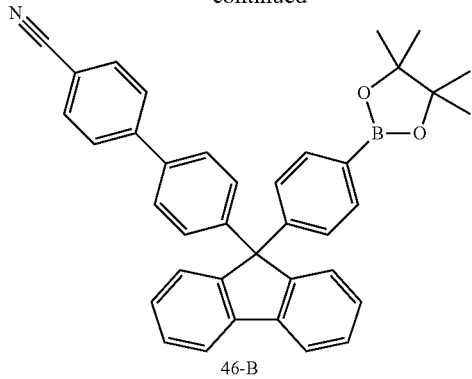

48

Preparation Example 13: Preparation of Compound 53

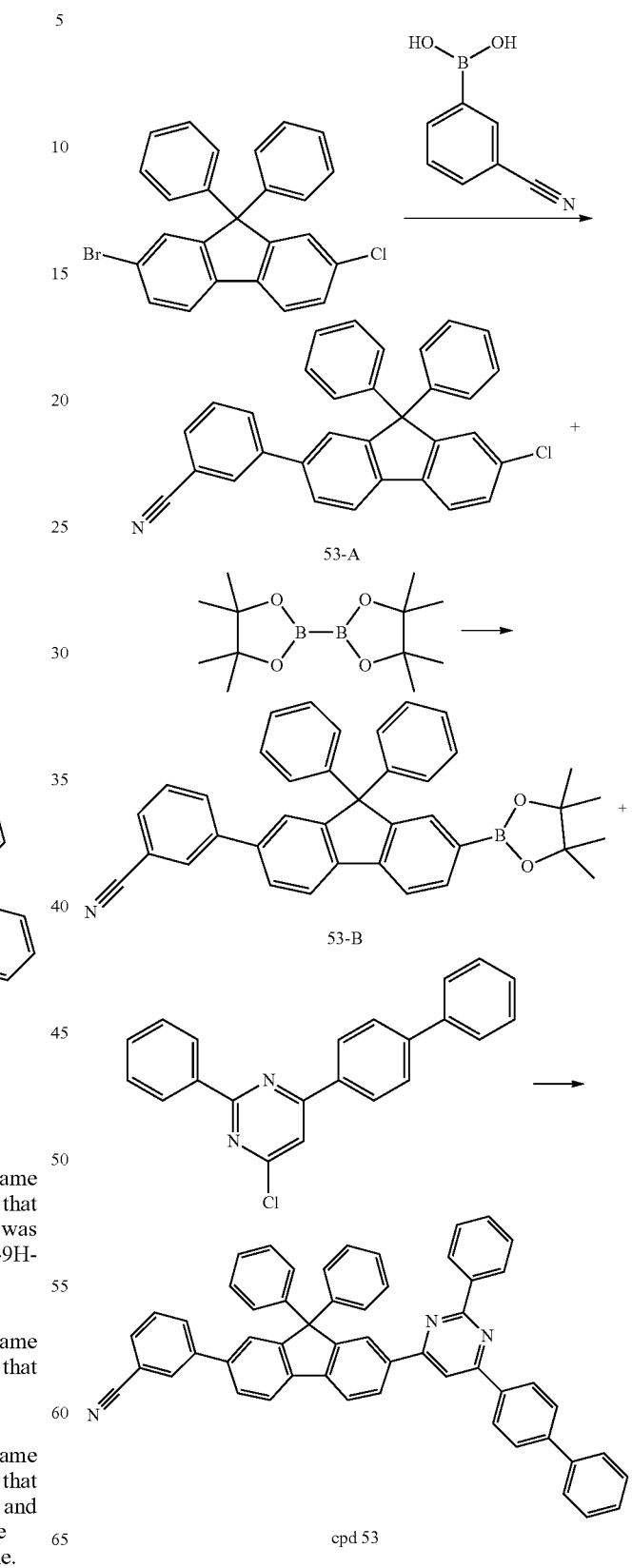

Compound 46-A shown above was prepared in the same manner as in preparation of Compound 1-A, except that 9-(4-bromophenyl)-9-(4-chlorophenyl)-9H-fluorene was used instead of 9-(3-bromophenyl)-9-(3-chlorophenyl)-9H-fluorene.

MS: $[M+H]^+=454$

Compound 46-B shown above was prepared in the same manner as in preparation of Compound 1-B, except that Compound 46-A was used instead of Compound 1-A.

MS: $[M+H]^+=546$

Compound 46 shown above was prepared in the same manner as in preparation of Compound 1, except that Compound 46-B was used instead of Compound 1-B, and 2-([1,1'-biphenyl]-3-yl)-4-chloro-6-phenyl-1,3,5-triazine was used instead of 2-chloro-4,6-diphenyl-1,3,5-triazine.

MS: $[M+H]^+=727$

Compound 53 shown above was prepared in the same manner as in preparation of Compound 28, except that 4-([1,1'-biphenyl]-4-yl)-6-chloro-2-phenylpyrimidine was used instead of 2-(3-bromo-phenyl)-4,6-diphenyl-1,3,5-triazine.

MS: [M+H]⁺=726

Preparation Example 14: Preparation of Compound 63

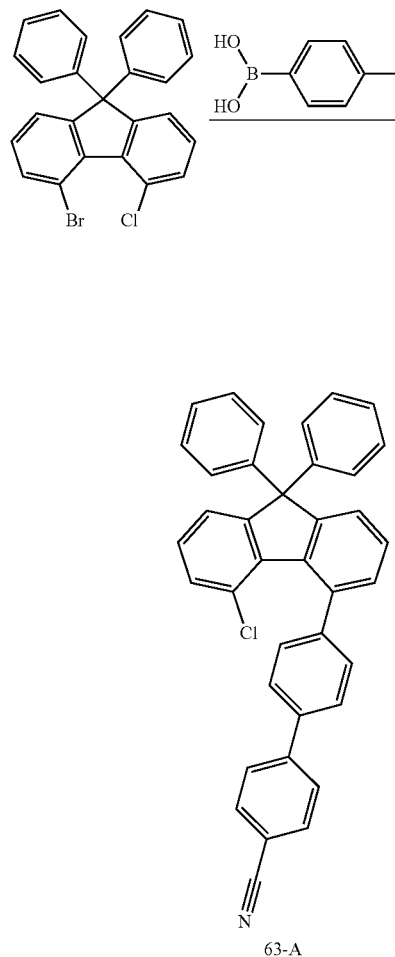

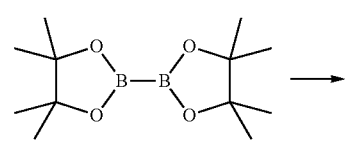

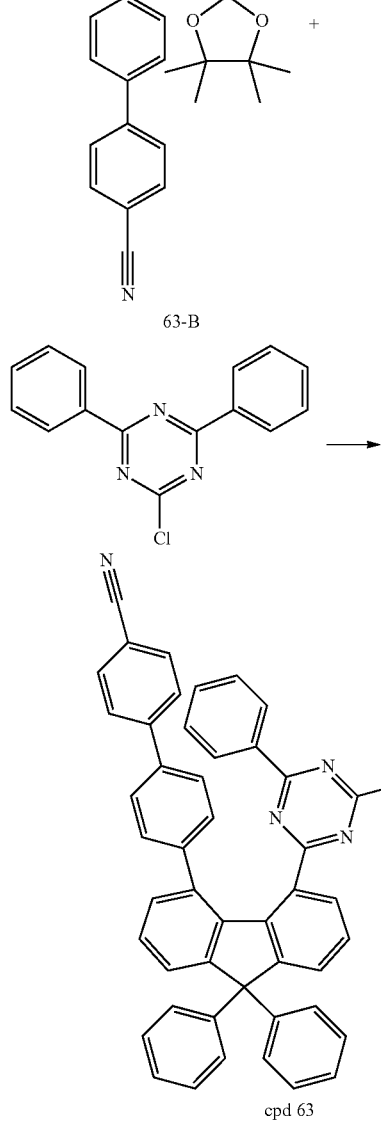

Compound 63-A shown above was prepared in the same manner as in preparation of Compound 1-A, except that 4-bromo-5-chloro-9,9-diphenyl-9H-fluorene was used instead of 9-(3-bromophenyl)-9-(3-chlorophenyl)-9H-fluorene, and (4'-cyano-[1,1'-biphenyl]-4-yl)-boronic acid was used instead of (4-cyanophenyl)boronic acid.

MS: [M+H]⁺=530

Compound 63-B shown above was prepared in the same manner as in preparation of Compound 1-B, except that Compound 63-A was used instead of Compound 1-A.

MS: [M+H]⁺=624

Compound 63 shown above was prepared in the same manner as in preparation of Compound 1, except that Compound 63-B was used instead of Compound 1-B.

MS: [M+H]⁺=727

Preparation Example 15: Preparation of Compound 78

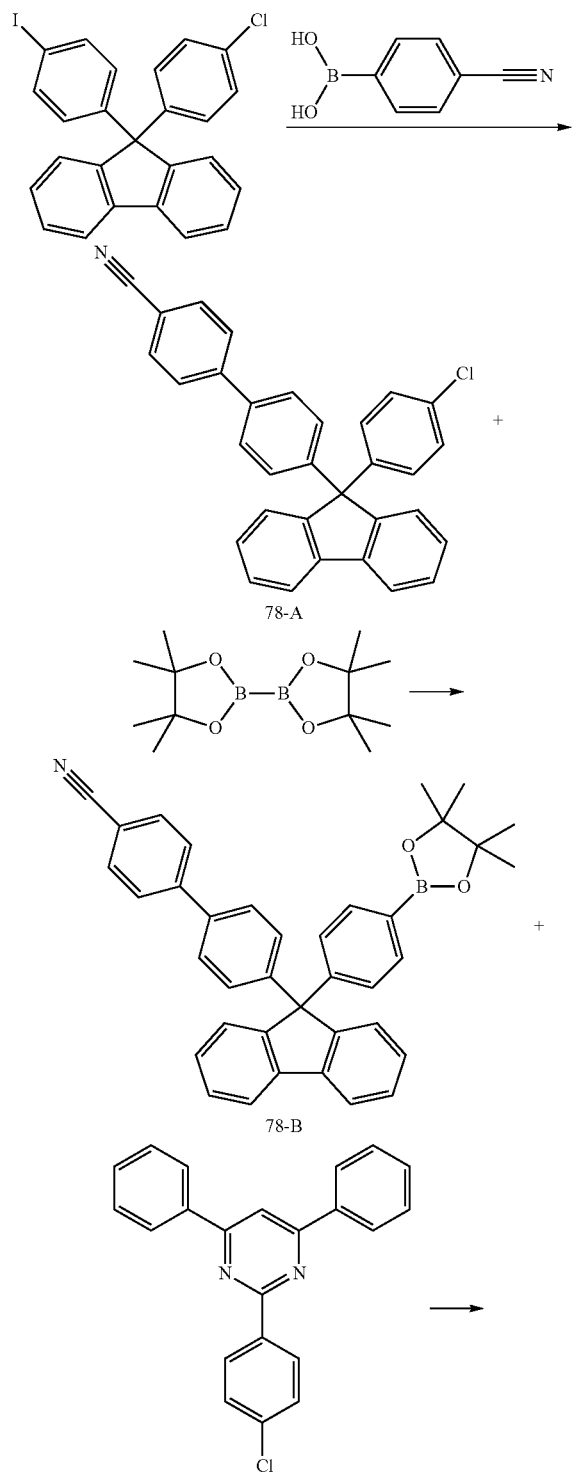

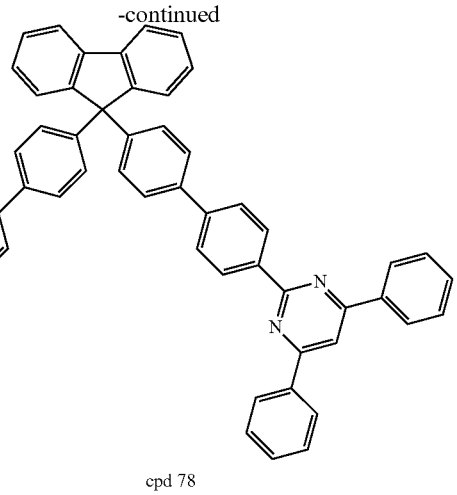

cpd 78

Compound 78-A shown above shown above was prepared in the same manner as in preparation of Compound 1-A, except that 9-(4-chlorophenyl)-9-(4-iodophenyl)-9H-fluorene was used instead of 9-(3-bromophenyl)-9-(3-chlorophenyl)-9H-fluorene.

MS: [M+H]⁺=454

Compound 78-B shown above was prepared in the same manner as in preparation of Compound 1-B, except that Compound 78-A was used instead of Compound 1-A.

MS: [M+H]⁺=546

Compound 78 shown above was prepared in the same manner as in preparation of Compound 1, except that Compound 78-B was used instead of Compound 1-B, and 2-(4-chlorophenyl)-4,6-diphenylpyrimidine was used instead of 2-chloro-4,6-diphenyl-1,3,5-triazine.

MS: [M+H]⁺=726

Preparation Example 16: Preparation of Compound 81

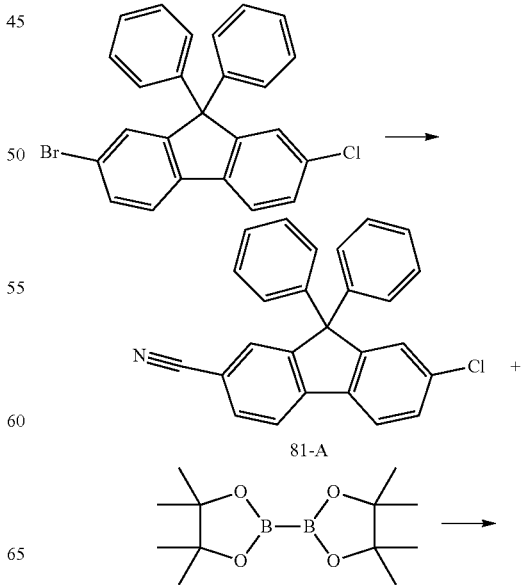

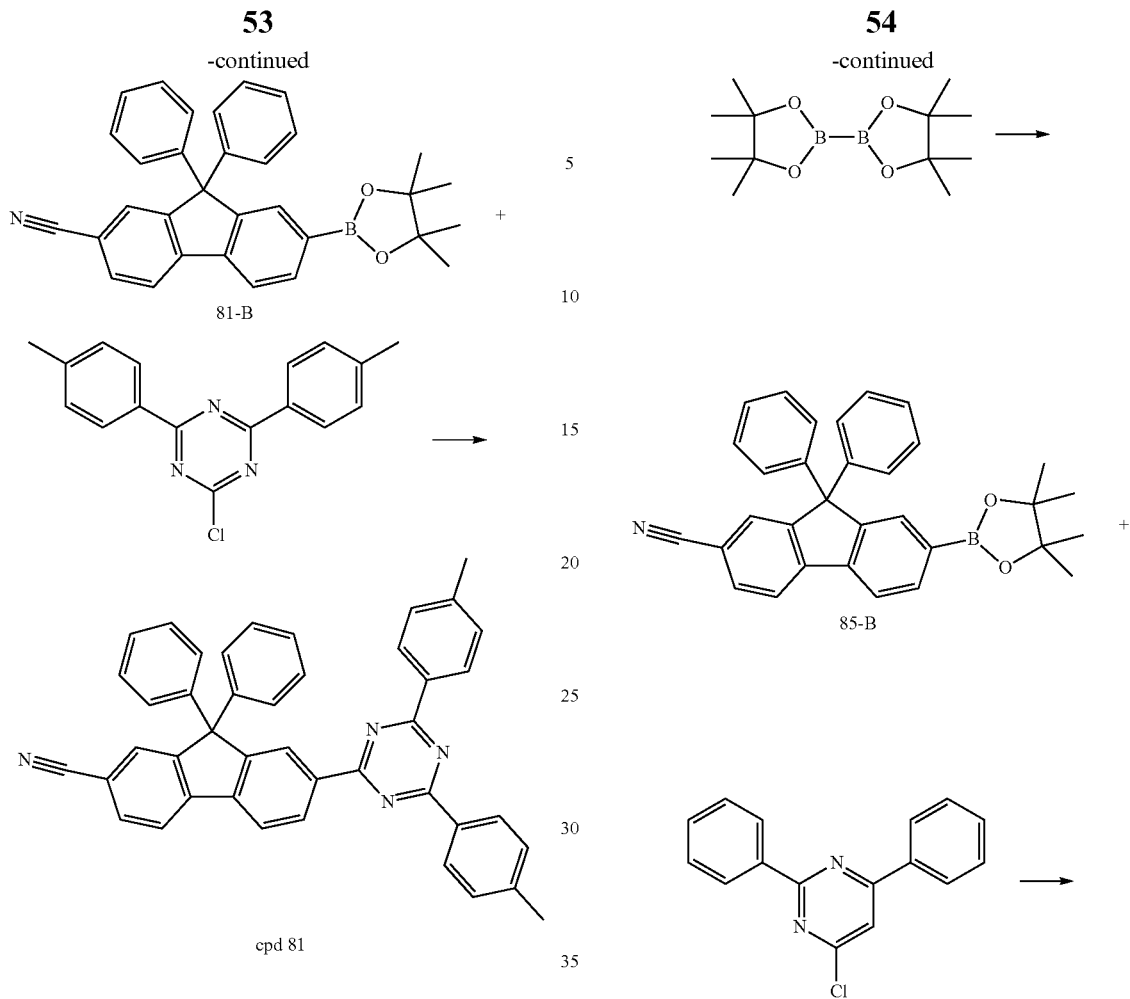

Compound 81 shown above was prepared in the same manner as in preparation of Compound 25, except that 2-chloro-4,6-di-p-tolyl-1,3,5-triazine was used instead of 2-chloro-4,6-diphenyl-1,3,5-triazine.

MS: [M+H]⁺=603

Preparation Example 17: Preparation of Compound 85

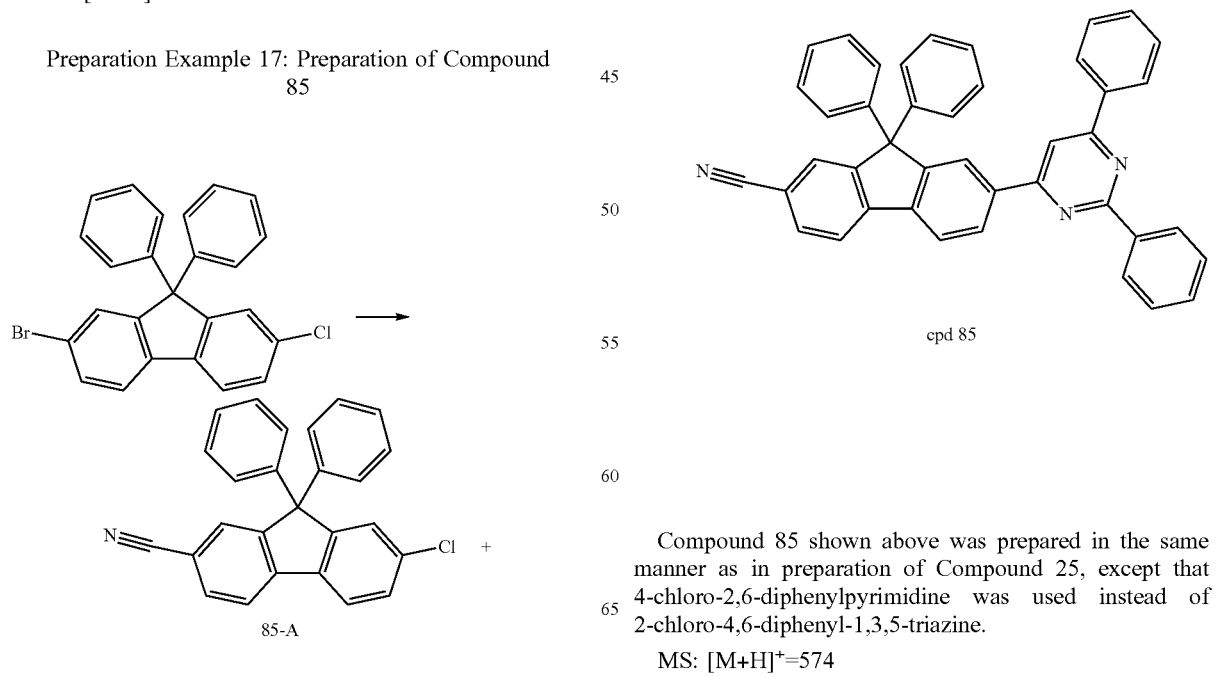

Compound 85 shown above was prepared in the same manner as in preparation of Compound 25, except that 4-chloro-2,6-diphenylpyrimidine was used instead of 2-chloro-4,6-diphenyl-1,3,5-triazine.

MS: [M+H]⁺=574

Preparation Example 18: Preparation of Compound 87

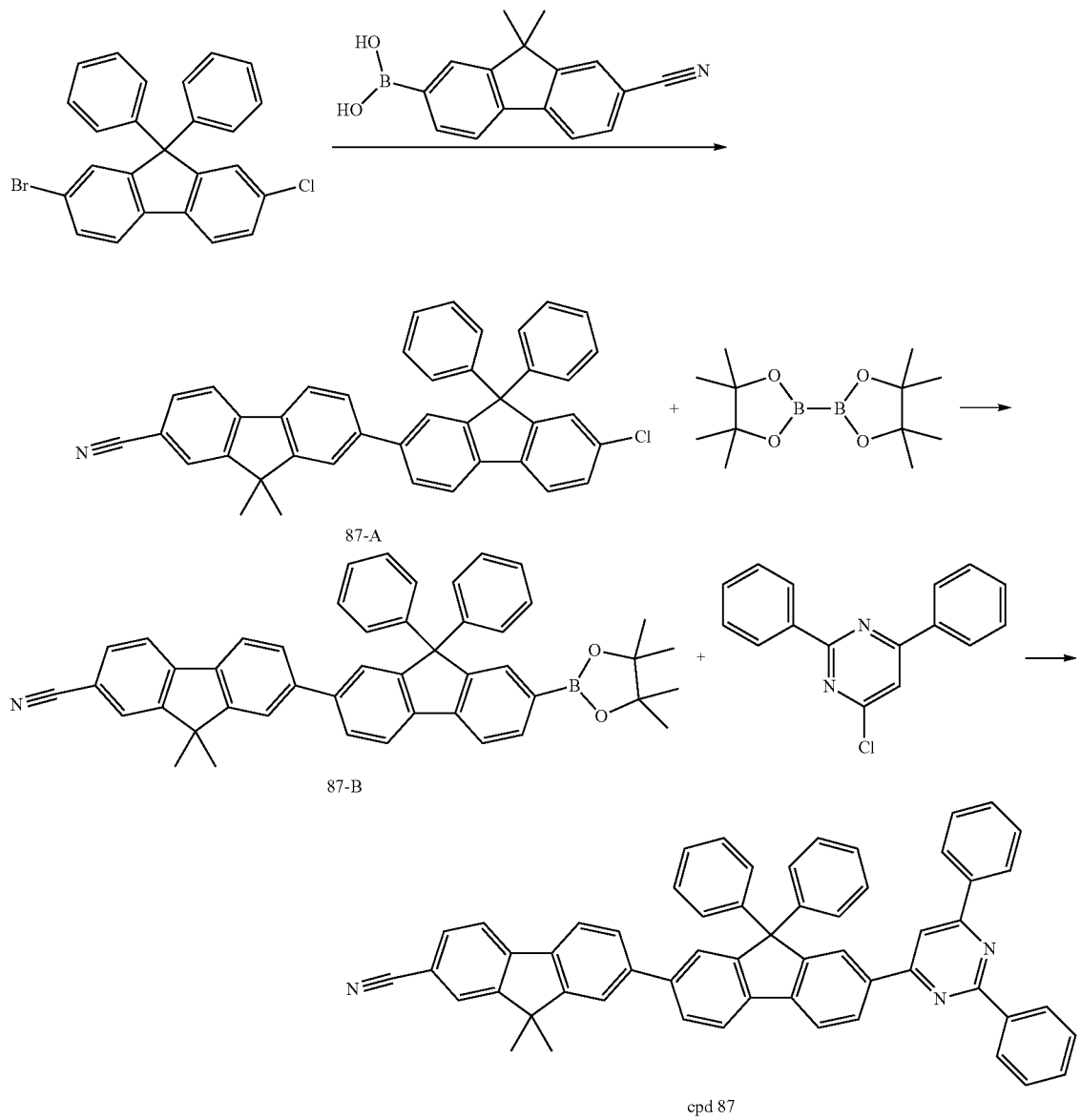

Compound 87-A shown above was prepared in the same manner as in preparation of Compound 1-A, except that (7-cyano-9,9-dimethyl-9H-fluoren-2-yl)boronic acid was used instead of (4-cyanophenyl)boronic acid.

MS: [M+H]$^+$=570

Compound 87-B shown above was prepared in the same manner as in preparation of Compound 1-B, except that Compound 87-A was used instead of Compound 1-A.

MS: [M+H]$^+$=662

Compound 87 shown above was prepared in the same manner as in preparation of Compound 1, except that Compound 87-B was used instead of Compound 1-B, and 4-chloro-2,6-diphenylpyrimidine was used instead of 2-chloro-4,6-diphenyl-1,3,5-triazine.

MS: [M+H]$^+$=766

EXAMPLES

Example 1

A glass substrate (Corning 7059 glass) coated with ITO (indium tin oxide) to a thin thickness of 1,000 Å was washed by ultrasonication with distilled water in which a detergent was dissolved. The detergent used herein was a product commercially available from Fischer Co. and the distilled water used herein was distilled water secondarily filtered through a filter commercially available from Millipore Co. ITO was washed for 30 minutes and was then ultrasonically washed with distilled water repeatedly twice for 10 minutes. After washing with distilled water, ultrasonic washing was conducted with isopropyl alcohol, acetone and methanol solvents in this order and then drying was conducted.

Hexanitrile hexaazatriphenylene was subjected to thermal vacuum deposition to a thickness of 500 Å on the ITO transparent electrode thus prepared, to form a hole injection layer. The following HT1 (400 Å) as a hole-transporting material was vacuum-deposited on the hole injection layer and the following HI (host) and the following D1 (dopant) as materials for a light emitting layer were vacuum-deposited to a thickness of 300 Å in a weight ratio of 95:5. Compound 1 prepared in Preparation Example 1 and LiQ were vacuum-deposited on the light emitting layer in a weight ratio of 7:3 to 3:7, to form an electron injection and transport layer with a thickness of 350 Å. Lithium fluoride (LiF) and aluminum were sequentially deposited to thicknesses of 12 Å and 2,000 Å, respectively, on the electron injection and transport layer, to form a cathode and thereby manufacture an organic light emitting device.

During the process, the deposition rate of organic materials was maintained at 0.4 to 0.7 Å/sec, the lithium fluoride of the cathode was maintained at a deposition rate of 0.3 Å/sec, aluminum was maintained at a deposition rate of 2 Å/sec, and the vacuum level during deposition was maintained at $2\times10^{-7}$ to $5\times10^{-6}$ torr, to manufacture the organic light emitting device. The compounds used for the process are given below.

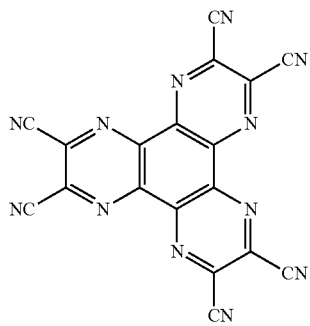

-continued

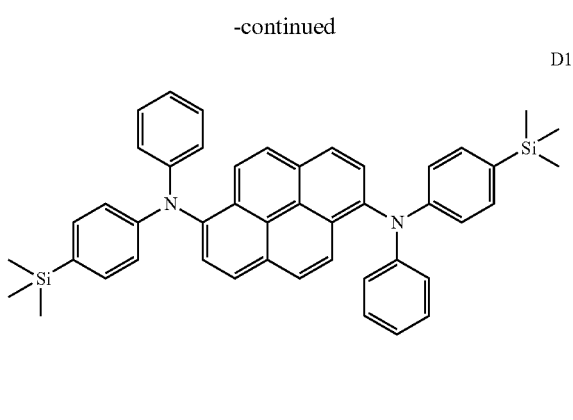

Examples 2 to 18

Organic light emitting devices were manufactured using the same process as in Example 1 except that the compound prepared in Preparation Example as shown in the following Table 1 was used as the compound for the electron injection and transport layer.

Comparative Examples 1 to 5

Organic light emitting devices were manufactured using the same process as in Example 1 except that the compound prepared in Preparation Example as shown in the following Table 1 was used as the compound for the electron injection and transport layer. In the following Table 1, the compounds of [ET 1] to [ET 5] are given below.

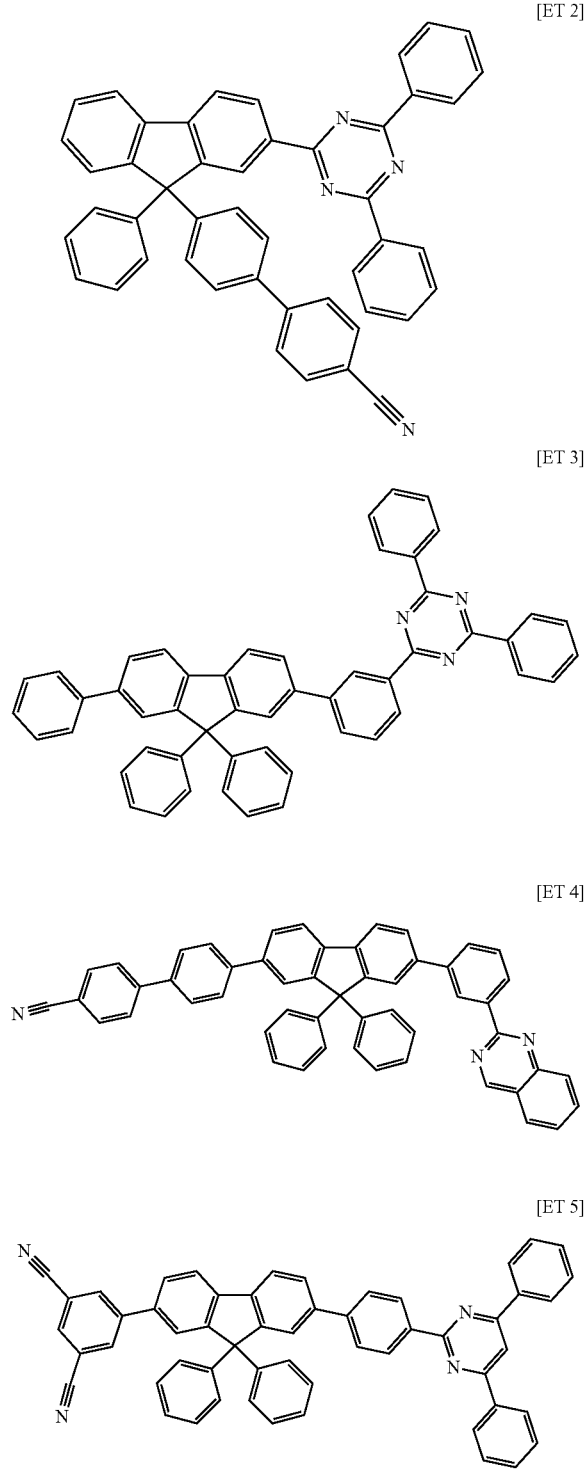

TABLE 1

| | Compound | Voltage (V) | Current efficiency (cd/A) | Chromaticity coordinates (x, y) | Lifetime (98% at 20 mA/cm²) |
|---|---|---|---|---|---|
| Example 1 | Compound 1 | 3.82 | 5.06 | (0.134, 0.126) | 196 |
| Example 2 | Compound 2 | 3.84 | 5.21 | (0.134, 0.126) | 177 |
| Example 3 | Compound 5 | 3.79 | 5.26 | (0.134, 0.126) | 231 |
| Example 4 | Compound 6 | 3.80 | 5.47 | (0.134, 0.126) | 207 |
| Example 5 | Compound 13 | 3.72 | 5.25 | (0.134, 0.126) | 214 |
| Example 6 | Compound 14 | 3.78 | 5.22 | (0.134, 0.127) | 191 |
| Example 7 | Compound 20 | 3.84 | 5.06 | (0.134, 0.126) | 201 |
| Example 8 | Compound 25 | 3.77 | 5.03 | (0.134, 0.126) | 180 |
| Example 9 | Compound 27 | 3.75 | 5.68 | (0.134, 0.126) | 178 |
| Example 10 | Compound 28 | 3.72 | 5.73 | (0.134, 0.126) | 172 |
| Example 11 | Compound 37 | 3.80 | 5.39 | (0.134, 0.126) | 185 |
| Example 12 | Compound 46 | 3.88 | 5.47 | (0.134, 0.126) | 210 |
| Example 13 | Compound 53 | 3.79 | 5.67 | (0.134, 0.126) | 198 |
| Example 14 | Compound 63 | 3.74 | 5.14 | (0.134, 0.126) | 173 |
| Example 15 | Compound 78 | 3.73 | 5.26 | (0.134, 0.127) | 200 |
| Example 16 | Compound 81 | 3.78 | 5.18 | (0.134, 0.127) | 168 |
| Example 17 | Compound 85 | 3.73 | 5.20 | (0.134, 0.126) | 202 |
| Example 18 | Compound 87 | 3.89 | 5.32 | (0.134, 0.126) | 210 |
| Comparative Example 1 | [ET 1] | 4.43 | 3.89 | (0.134, 0.127) | 117 |
| Comparative Example 2 | [ET 2] | 4.54 | 3.87 | (0.135, 0.127) | 128 |
| Comparative Example 3 | [ET 3] | 4.36 | 3.88 | (0.135, 0.126) | 104 |
| Comparative Example 4 | [ET 4] | 4.62 | 3.60 | (0.134, 0.126) | 120 |
| Comparative Example 5 | [ET 5] | 4.67 | 3.75 | (0.134, 0.126) | 130 |

The driving voltage and luminous efficiency of the organic light emitting devices manufactured in Examples and Comparative Examples were measured at a current density of 10 mA/cm², and LT97, which means the time, at which the present brightness corresponded to 98% of the initial brightness, was measured at a current density of 20 mA/cm². Results are shown in the following Table 1.

As can be seen from Table 1, the compounds of Examples 1 to 18 using the compound of Chemical Formula 1 according to the present invention for electron injection and control layers of organic light emitting devices exhibited low driving voltage, high efficiency and long lifetime characteristics, as compared to the compounds of Comparative Examples 1 to 5.

In particular, it can be seen that, as compared to the case in which a heteroaryl group and an aryl-CN group are symmetrically bonded to two sides of the fluorene group, Comparative Examples 1 and 2 exhibited bad J-V characteristics, high (off) voltage, low efficiency and short lifetime. In addition, it can be seen that Comparative Example 3 not having a —CN group exhibited considerably short lifetime, as compared to the compound having the structure of Chemical Formula 1 having a —CN group. In addition, it can be seen that the compound, in which the heteroaryl group linked to one side of the fluorene group is a hetero group excluding triazine and pyrimidine, exhibited high driving voltage and low efficiency, as compared to the compound having the structure of Chemical Formula 1 according to the present invention. Finally, it can be seen that materials substituted by two or more —CN groups exhibited considerably high driving voltage and low efficiency, as compared to the compound having the structure of Chemical Formula 1.

The invention claimed is:

1. A fluorene derivative of any one of Chemical Formulae 7 to 9:

[Chemical Formula 7]

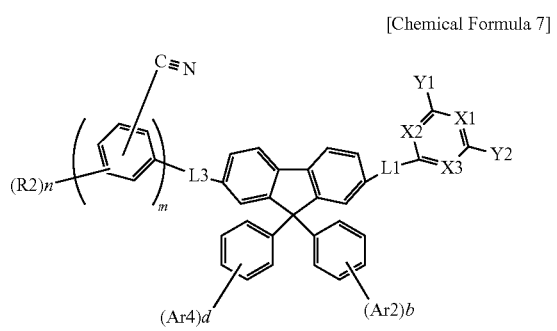

[Chemical Formula 8]

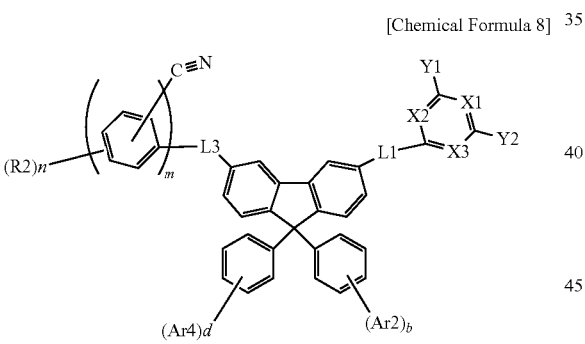

[Chemical Formula 9]

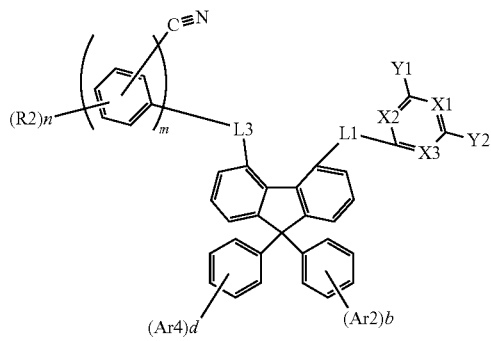

wherein:
L1 is a direct bond, a naphthylene group, or a phenylene group that is unsubstituted or substituted by an alkyl group;
L3 is a direct bond, a phenylene group, a biphenylene group, a naphthylene group, a phenanthrene group, a divalent fluorene group that is unsubstituted or substituted by an alkyl group, or a divalent fluorene group that is unsubstituted or substituted by an aryl group;
L5 is a phenylene group, a biphenylene group, a naphthylene group, a phenanthrene group, a divalent fluorene group that is unsubstituted or substituted by an alkyl group, or a divalent fluorene group that is unsubstituted or substituted by an aryl group;
Ar2 and Ar4 are hydrogen;
b and d are each 5;
X1 to X3 are identical to or different from one another, and are each independently N or CR1, wherein two or more of X1 to X3 are N;
R1 and R2 are identical to or different from one another, and are each independently hydrogen or deuterium;
Y1 and Y2 are identical to or different from one another, and are each independently hydrogen, deuterium, or an aryl group having 6 to 20 atoms that is unsubstituted or substituted with an alkyl group;
n is an integer of 0 to 4, in which, when n is 2 or more, R2 are identical to or different from each other;
m is 1.

2. The fluorene derivative of claim 1, wherein Y1 or Y2 is an aryl group having 6 to 20 carbon atoms.

3. A fluorene derivative selected from among the following compounds:

cpd 5

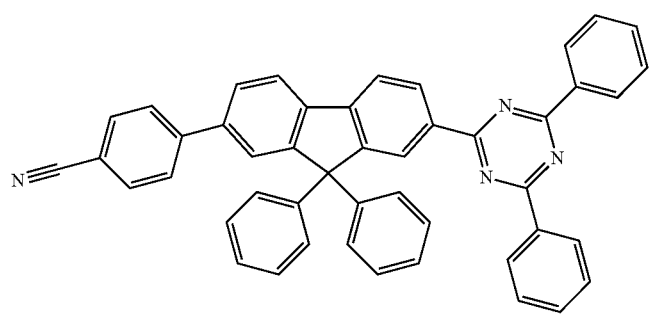

cpd 6
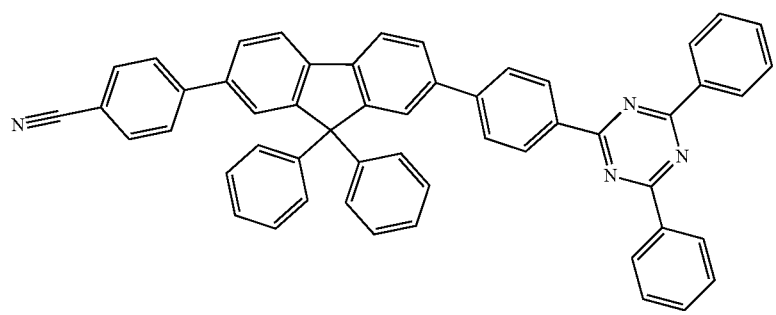
cpd 7
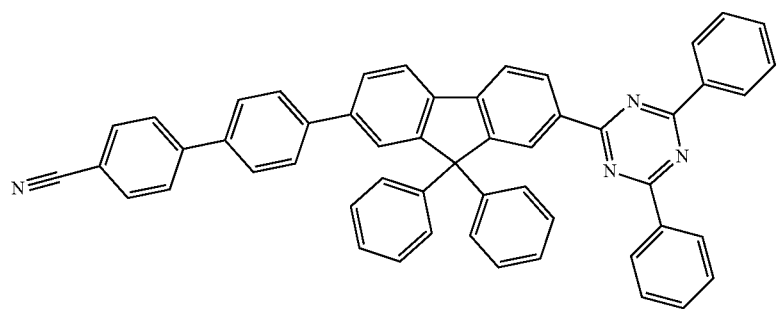
cpd 8
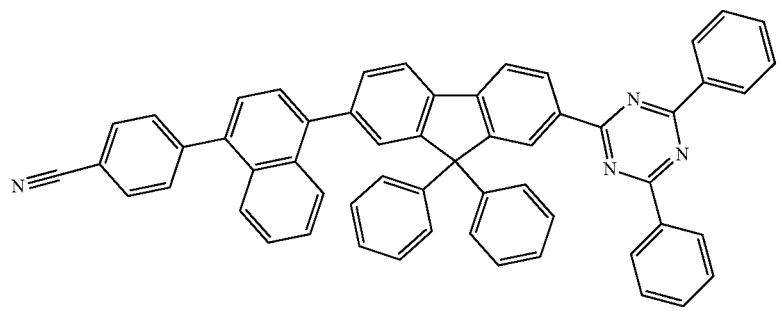
cpd 13
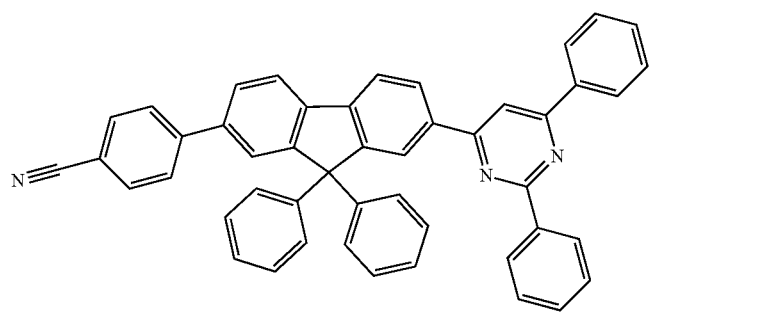
cpd 14
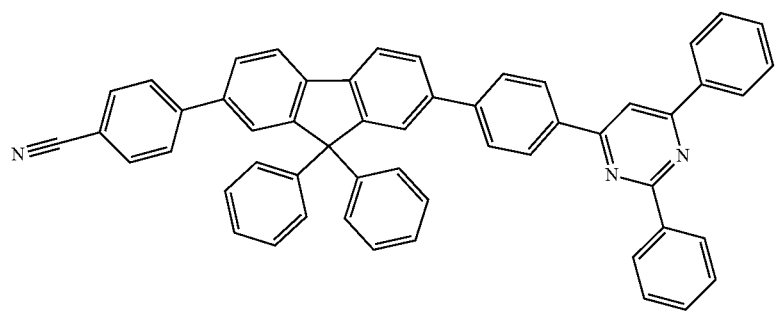

-continued
cpd 15
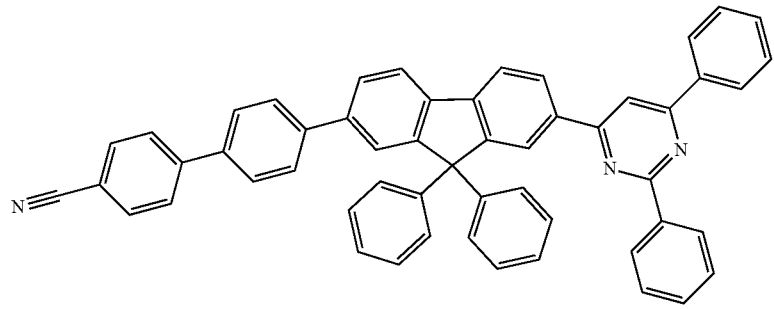
cpd 16
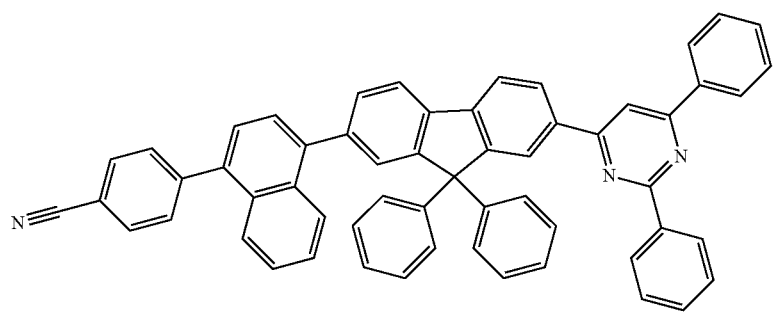
cpd 21
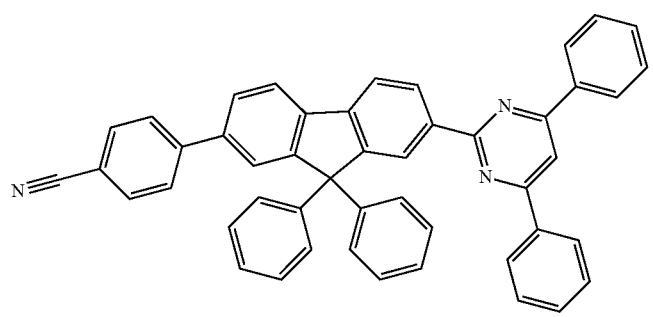
cpd 22
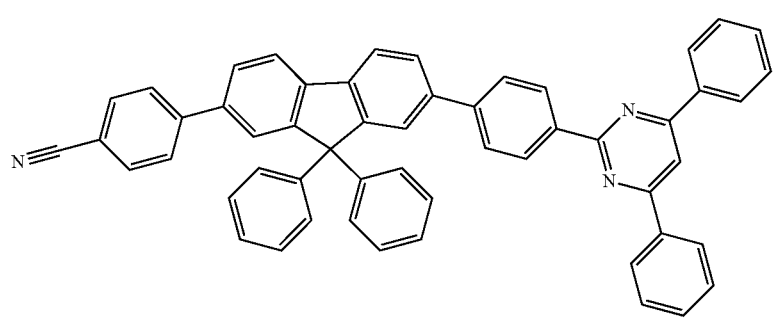
cpd 23
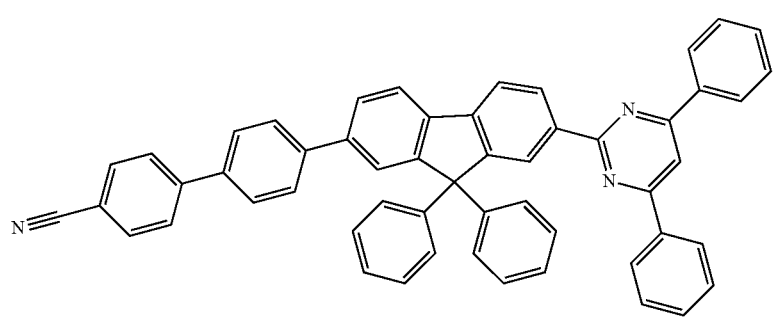

-continued
cpd 24
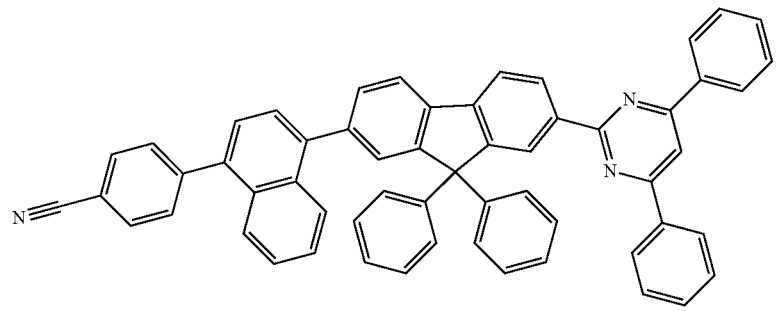
cpd 26
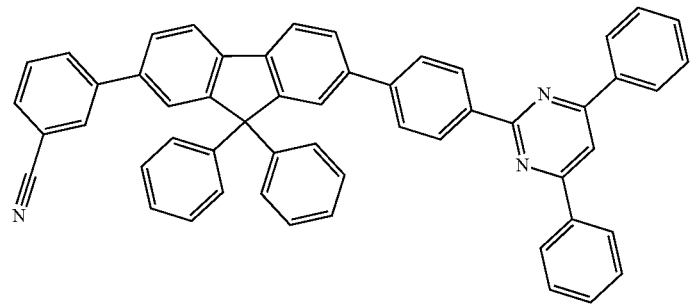
cpd 27
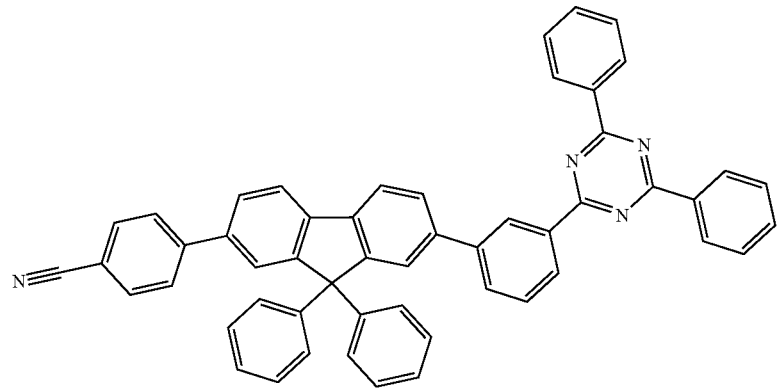
cpd 28
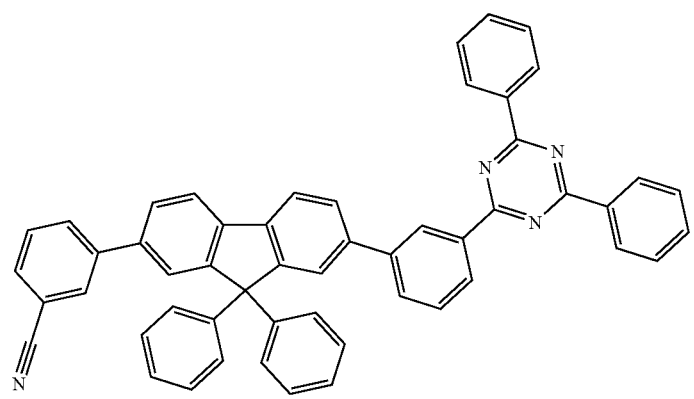

-continued
cpd 31
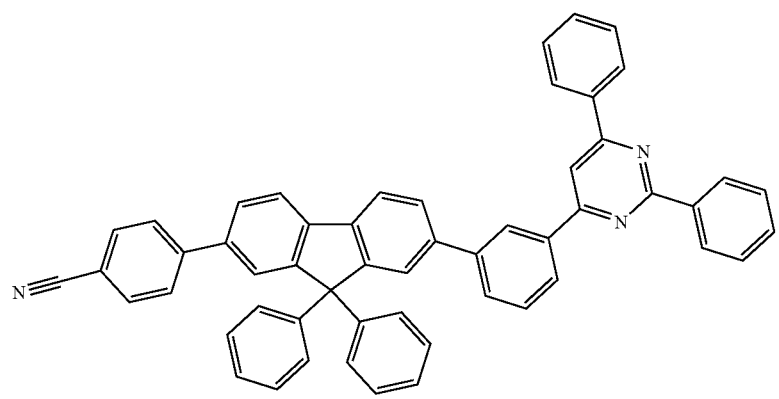
cpd 37
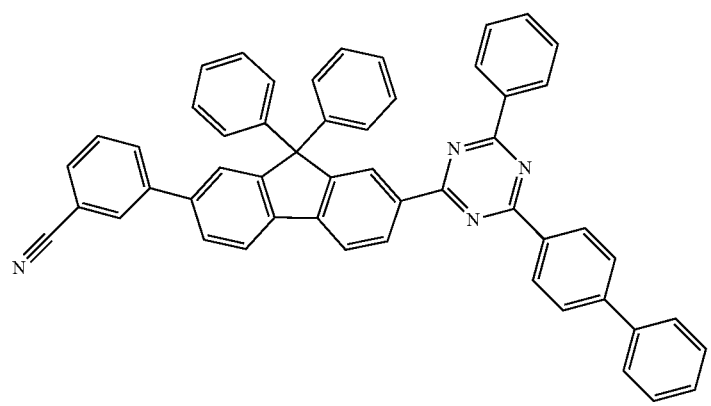
cpd 38
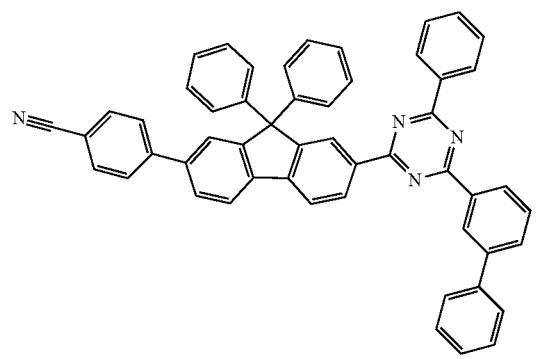
cpd 39
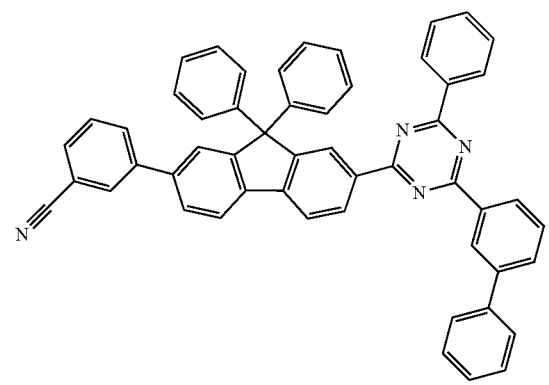
cpd 40
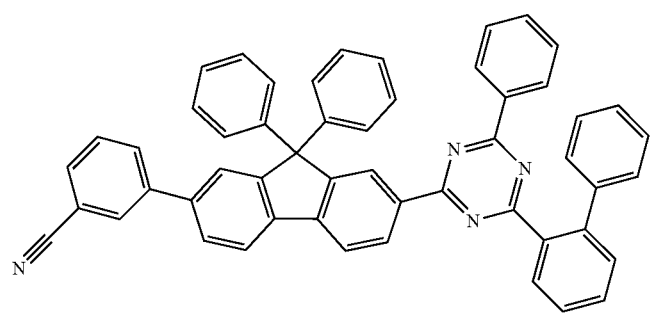

-continued
cpd 51
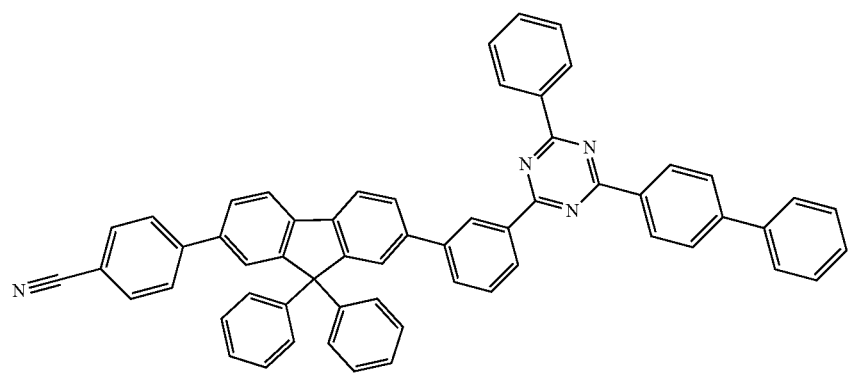
cpd 52
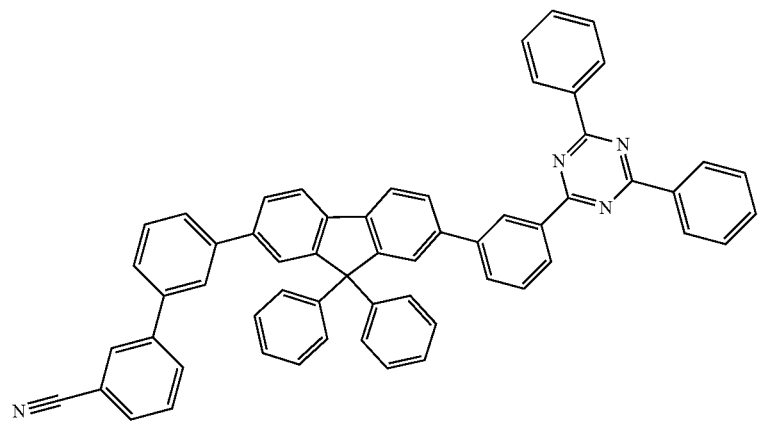
cpd 53
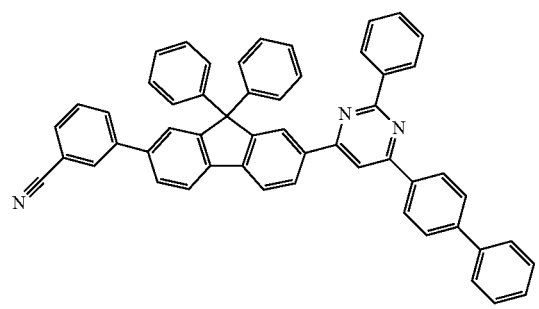
cpd 54
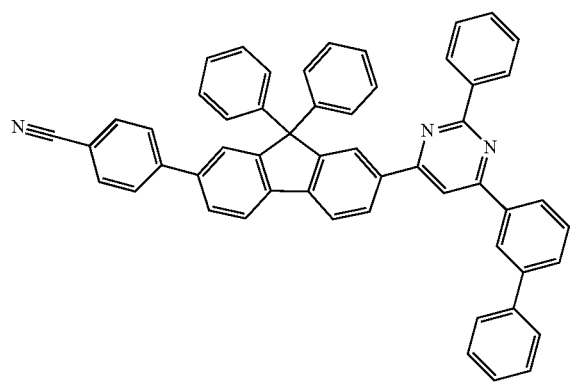
cpd 55
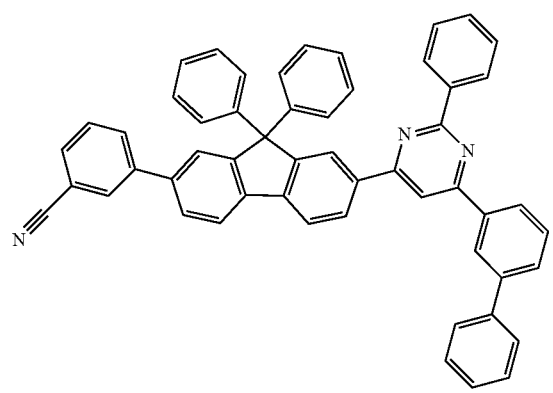
cpd 56

-continued
cpd 63
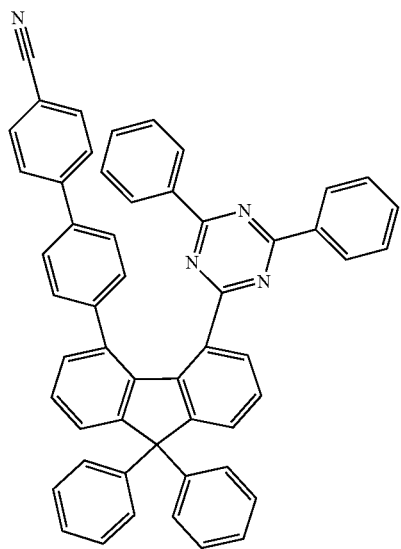
cpd 64
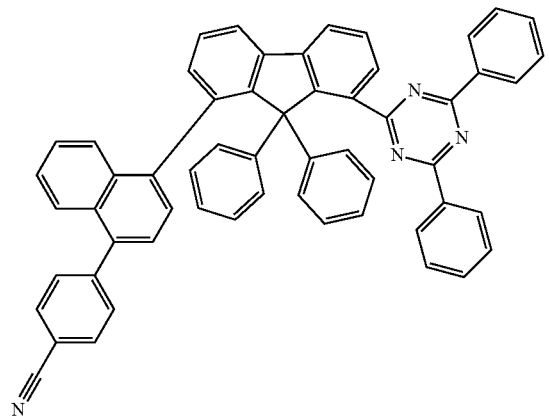
cpd 65
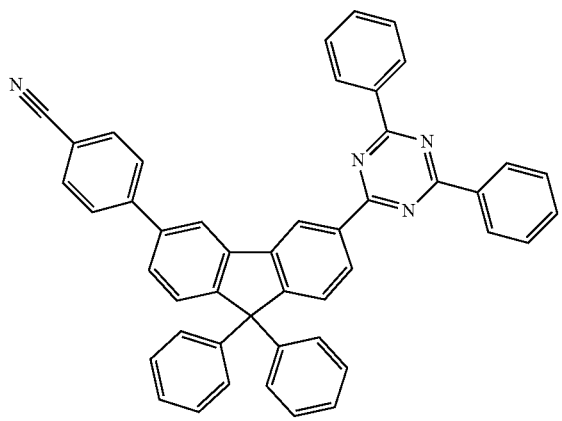
cpd 66
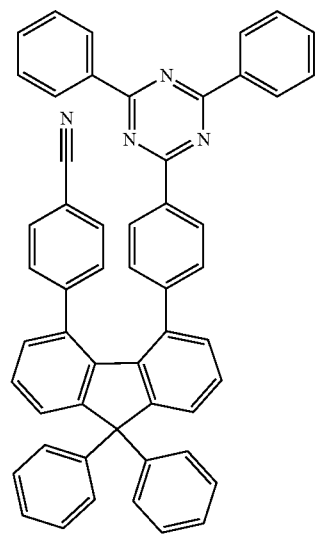
cpd 68
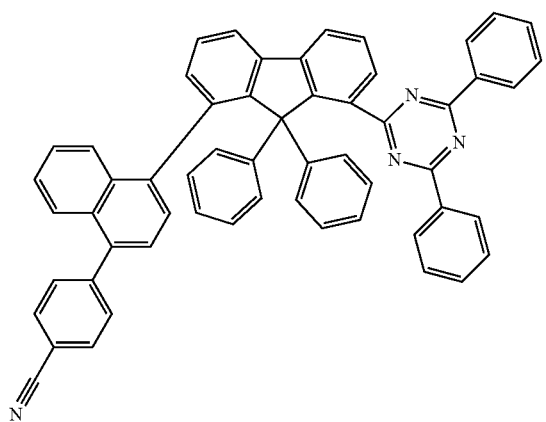
cpd 69
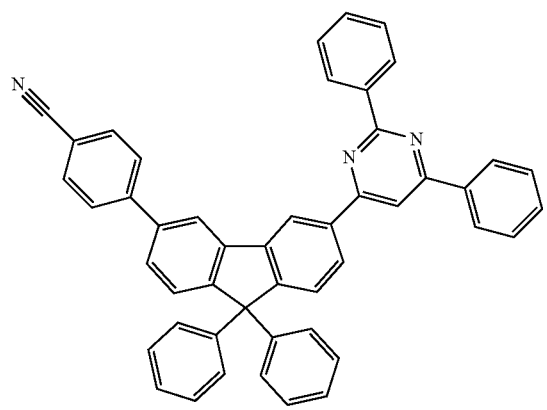

-continued
cpd 72
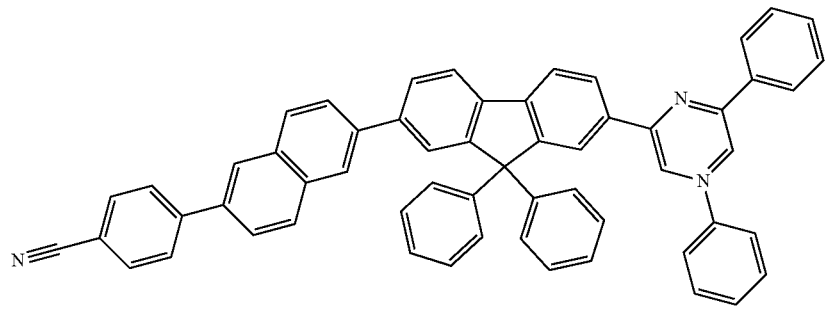
cpd 73
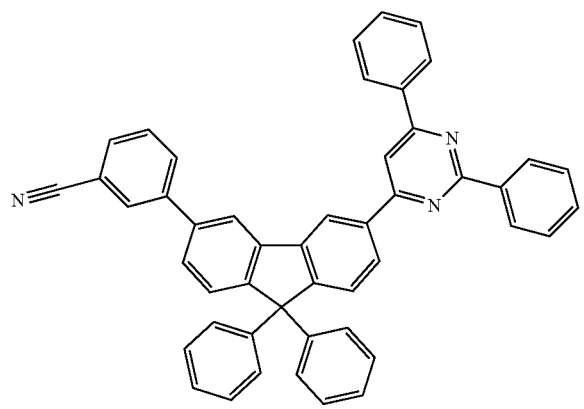
cpd 74
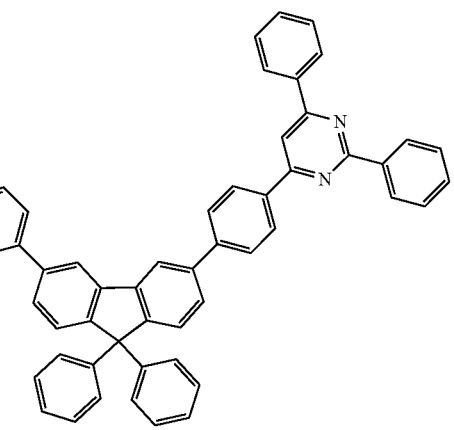
cpd 76
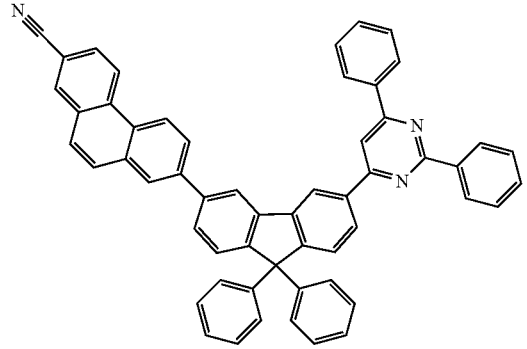
cpd 79
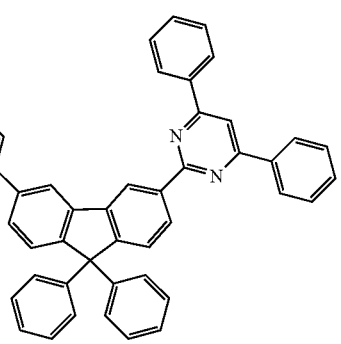
cpd 82
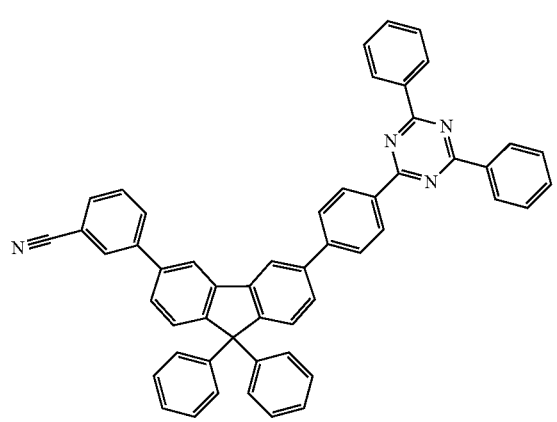
cpd 83
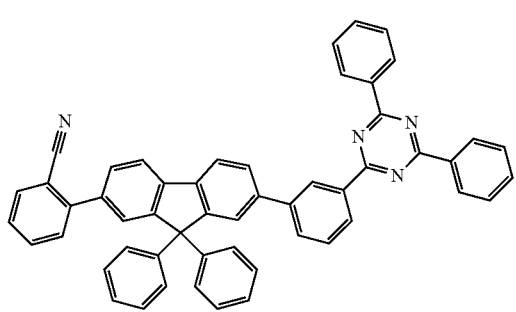

-continued

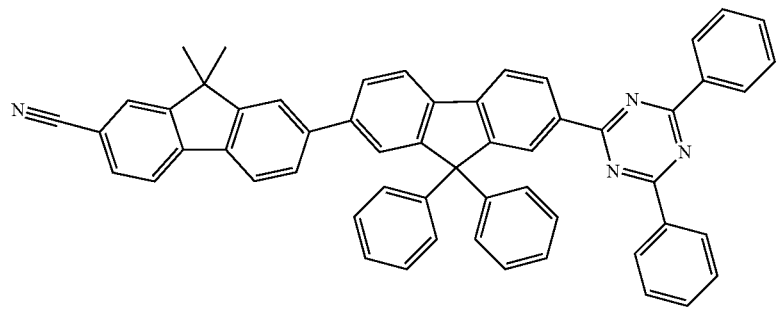
cpd 84

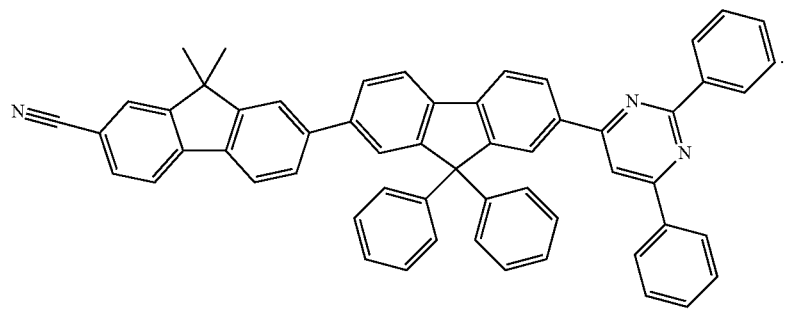
cpd 87

4. An organic light emitting device comprising:
a first electrode;
a second electrode facing the first electrode; and
at least one organic material layer interposed between the first electrode and the second electrode,
wherein the at least one organic material layer comprises the fluorene derivative of claim 1.

5. The organic light emitting device of claim 4, wherein the organic material layer comprises a light emitting layer,
wherein the light emitting layer comprises the fluorene derivative.

6. The organic light emitting device of claim 4, wherein the organic material layer comprises a hole injection layer or a hole transport layer,
wherein the hole injection layer or the hole transport layer comprises the fluorene derivative.

7. The organic light emitting device of claim 4, wherein the organic material layer comprises an electron injection layer, an electron transport layer, or an electron injection and transport layer,
wherein the electron injection layer, the electron transport layer, or the electron injection and transport layer comprises the fluorene derivative.

8. The fluorene derivative of claim 1, wherein L1 is each independently a naphthylene group or a phenylene group that is unsubstituted or substituted by an alkyl group having 1 to 10 carbon atoms.

9. The fluorene derivative of claim 1, wherein Y1 and Y2 are identical to or different from one another, and are each independently a biphenyl group or a phenyl group that is unsubstituted or substituted by an alkyl group having 1 to 10 carbon atoms.

10. An organic light emitting device comprising:
a first electrode;
a second electrode facing the first electrode; and
at least one organic material layer interposed between the first electrode and the second electrode,
wherein the at least one organic material layer comprises the fluorene derivative of claim 5.

11. The organic light emitting device of claim 10, wherein the organic material layer comprises a light emitting layer, and the light emitting layer comprises the fluorene derivative.

12. The organic light emitting device of claim 10, wherein the organic material layer comprises a hole injection layer or a hole transport layer, and the hole injection layer or the hole transport layer comprises the fluorene derivative.

13. The organic light emitting device of claim 10, wherein the organic material layer comprises an electron injection layer, an electron transport layer, or an electron injection and transport layer, and the electron injection layer, the electron transport layer, or the electron injection and transport layer comprises the fluorene derivative.

* * * * *